(12) United States Patent
Geusen

(10) Patent No.: US 9,066,828 B2
(45) Date of Patent: Jun. 30, 2015

(54) ENDOVASCULAR DELIVERY SYSTEM WITH FLEXIBLE AND TORQUEABLE HYPOTUBE

(71) Applicant: TriVascular, Inc., Santa Rosa, CA (US)

(72) Inventor: Mark Geusen, Santa Rosa, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 70 days.

(21) Appl. No.: 13/803,062

(22) Filed: Mar. 14, 2013

(65) Prior Publication Data
US 2013/0338753 A1    Dec. 19, 2013

Related U.S. Application Data

(60) Provisional application No. 61/660,103, filed on Jun. 15, 2012.

(51) Int. Cl.
| | |
|---|---|
| A61F 2/06 | (2013.01) |
| A61F 2/954 | (2013.01) |
| A61F 2/966 | (2013.01) |
| A61M 25/00 | (2006.01) |
| A61B 17/00 | (2006.01) |
| A61M 25/06 | (2006.01) |

(52) U.S. Cl.
CPC .......... *A61F 2/954* (2013.01); *A61F 2/966* (2013.01); *A61M 25/0054* (2013.01); *A61B 2017/00309* (2013.01); *A61M 2025/0004* (2013.01); *A61M 25/0051* (2013.01); *A61M 2025/0681* (2013.01)

(58) Field of Classification Search
CPC .... A61F 2/954; A61F 2/966; A61M 25/0054; A61M 25/00511; A61M 25/01; A61M 25/0138; A61M 25/0141; A61M 25/0013; A61M 25/0015; A61M 25/0045; A61M 25/0046; A61M 2025/0004; A61M 2025/0681; A61M 2025/0062; A61M 2025/0047; A61B 2017/00309

USPC .............. 623/1.11, 1.35, 1.36; 606/108, 159, 606/192, 200; 600/585, 435; 604/171, 523, 604/525, 534, 96.01, 528, 95.04

See application file for complete search history.

(56) References Cited

U.S. PATENT DOCUMENTS

| | | | | |
|---|---|---|---|---|
| 4,636,313 A | * | 1/1987 | Vaillancourt | 210/436 |
| 5,114,399 A | * | 5/1992 | Kovalcheck | 604/22 |

(Continued)

FOREIGN PATENT DOCUMENTS

EP    0889252 A2    1/1999

OTHER PUBLICATIONS

PCT Search Report and Written Opinion for PCT/US2012/043623 dated Nov. 14, 2013.

*Primary Examiner* — Jocelin Tanner
(74) *Attorney, Agent, or Firm* — Hoffmann & Baron, LLP

(57) ABSTRACT

A medical device includes an elongate metallic hypotube having an open proximal end and an opposed open distal end defining a tubular wall having an open internal diameter and an exterior diameter. The tubular wall has a first flexible portion disposed near the proximal open end and a second portion disposed near the distal open end. The first flexible portion of the hypotube includes a plurality of slots extending through the tubular wall and having a circumferential arc from about 150° to about 300°; and where adjacent slots are axially offset from one and the other from about 30° to about 60°. The medical device may be used as part of an endovascular delivery system.

22 Claims, 15 Drawing Sheets

(56) References Cited

U.S. PATENT DOCUMENTS

| | | |
|---|---|---|
| 5,429,136 A | 7/1995 | Milo et al. |
| 5,507,732 A | 4/1996 | McClure et al. |
| 5,573,520 A | 11/1996 | Schwartz et al. |
| 5,716,373 A | 2/1998 | Wolvek et al. |
| 5,741,429 A | 4/1998 | Donadio, III et al. |
| 6,027,863 A | 2/2000 | Donadio, III |
| 6,107,004 A | 8/2000 | Donadio, III |
| 6,398,802 B1 | 6/2002 | Yee |
| 7,018,346 B2 | 3/2006 | Griffin et al. |
| 7,169,163 B2 | 1/2007 | Becker et al. |
| 7,208,001 B2 | 4/2007 | Coyle et al. |
| 7,220,266 B2 | 5/2007 | Gambale |
| 7,316,708 B2 | 1/2008 | Gordon et al. |
| 7,507,230 B2 | 3/2009 | Li et al. |
| 7,682,365 B2 | 3/2010 | Guinan |
| 7,867,271 B2 | 1/2011 | Geiser et al. |
| 7,989,042 B2 | 8/2011 | Obara et al. |
| 8,758,421 B2 | 6/2014 | Gerdts et al. |
| 2002/0029076 A1 | 3/2002 | Yee |
| 2002/0068966 A1 | 6/2002 | Holman et al. |
| 2002/0099432 A1 | 7/2002 | Yee |
| 2002/0151953 A1* | 10/2002 | Chobotov et al. ............ 623/1.11 |
| 2002/0193782 A1 | 12/2002 | Ellis et al. |
| 2003/0114776 A1 | 6/2003 | Griffin et al. |
| 2003/0144657 A1* | 7/2003 | Bowe et al. ..................... 606/41 |
| 2003/0167062 A1 | 9/2003 | Gambale et al. |
| 2003/0171760 A1 | 9/2003 | Gambale |
| 2003/0233068 A1* | 12/2003 | Jayaraman ................ 604/96.01 |
| 2004/0049256 A1 | 3/2004 | Yee |
| 2004/0064083 A1 | 4/2004 | Becker et al. |
| 2004/0064150 A1 | 4/2004 | Becker |
| 2004/0111095 A1 | 6/2004 | Gordon et al. |
| 2005/0113902 A1 | 5/2005 | Geiser et al. |
| 2005/0182475 A1 | 8/2005 | Jen et al. |
| 2006/0020320 A1* | 1/2006 | Shaolian et al. ............. 623/1.11 |
| 2006/0100687 A1* | 5/2006 | Fahey et al. ................. 623/1.11 |
| 2006/0121218 A1* | 6/2006 | Obara et al. .................. 428/34.7 |
| 2006/0241564 A1* | 10/2006 | Corcoran et al. ............. 604/523 |
| 2007/0073269 A1 | 3/2007 | Becker |
| 2007/0093858 A1 | 4/2007 | Gambale et al. |
| 2007/0135763 A1 | 6/2007 | Musbach et al. |
| 2007/0208351 A1 | 9/2007 | Turner et al. |
| 2007/0208405 A1 | 9/2007 | Goodin et al. |
| 2008/0077085 A1 | 3/2008 | Eidenschink et al. |
| 2008/0109059 A1 | 5/2008 | Gordon et al. |
| 2008/0114390 A1 | 5/2008 | Guinan |
| 2008/0172033 A1 | 7/2008 | Keith et al. |
| 2008/0188800 A1 | 8/2008 | Bencini et al. |
| 2009/0125097 A1 | 5/2009 | Bruszewski et al. |
| 2009/0143769 A1 | 6/2009 | Parodi et al. |
| 2009/0143771 A1 | 6/2009 | Casey et al. |
| 2010/0069882 A1 | 3/2010 | Jennings et al. |
| 2010/0204774 A1 | 8/2010 | Goodin et al. |
| 2011/0022069 A1 | 1/2011 | Mitusina |
| 2012/0053419 A1 | 3/2012 | Bloom |
| 2012/0123395 A1 | 5/2012 | Stoy et al. |

* cited by examiner

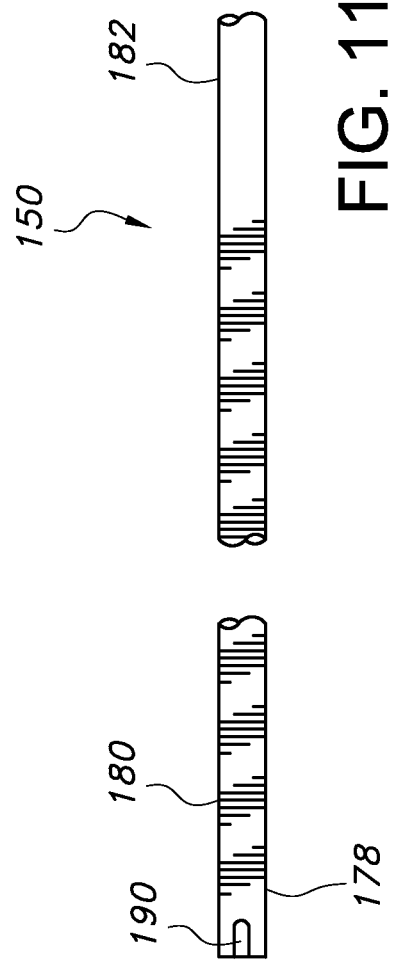
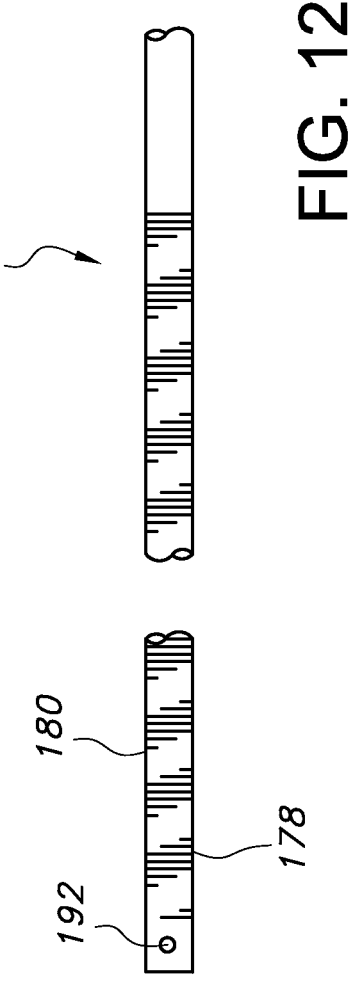
FIG. 11
FIG. 12

ENDOVASCULAR DELIVERY SYSTEM WITH FLEXIBLE AND TORQUEABLE HYPOTUBE

CROSS-REFERENCE TO RELATED APPLICATIONS

This application claims the benefit of U.S. Provisional Application No. 61/660,103, filed Jun. 15, 2012, the contents of which are incorporated by reference herein.

FIELD OF THE INVENTION

The present invention is related to an endovascular delivery system for an endovascular prosthesis. More particularly, the present invention is related to an endovascular delivery system having a slotted hypotube for flexibility and torqueability for an inflatable and bifurcated endovascular prosthesis.

BACKGROUND OF THE INVENTION

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M.D., published in 1986 by W.B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the Endurant™ and Talent™ Abdominal Stent Grafts sold by Medtronic, Inc. of Minneapolis, Minn.; the Zenith Flex® AAA Endovascular Graft and the Zenith TX2® TAA Endovascular Graft, both sold by Cook Medical, Inc. of Bloomington, Ind.; the AFX™ Endovascular AAA system sold by Endologix, Inc. of Irvine, Calif.; and the Gore® Excluder® AAA Endoprosthesis sold by W.L. Gore & Associates, Inc. of Flagstaff, Ariz. A commercially available stent graft for the treatment of TAAs is the Gore® TAG® Thoracic Endoprosthesis sold by W.L. Gore & Associates, Inc. of Flagstaff, Ariz.

When deploying devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process. In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated. What have been needed are stent graft systems, delivery systems and methods that are adaptable to a wide range of patient anatomies and that can be safely and reliably deployed using a flexible low profile system.

SUMMARY OF THE INVENTION

In one aspect of the present invention an endovascular delivery system is provided. The endovascular delivery system may include an elongate outer tubular sheath having an open lumen and opposed proximal and distal ends with a medial portion therein between; an elongate inner metallic hypotube having a tubular wall with an open lumen and opposed proximal and distal ends with a medial portion therein between, the hypotube having a longitudinal length greater than a longitudinal length of the outer tubular sheath, the hypotube being slidably disposed within the open lumen of the outer tubular sheath; the distal end of the outer tubular sheath being slidably disposed past and beyond the distal end of the hypotube to define an endovascular prosthesis delivery state and slidably retractable to the medial portion of the hypotube to define an endovascular prosthesis unsheathed state; where the hypotube further includes: a first flexible portion disposed from about the distal end of the hypotube to about the medial portion of the hypotube; a second portion disposed from about the medial portion of the hypotube to about the proximal end of the hypotube; the first flexible portion of the hypotube including a plurality of slots extending through the tubular wall of the hypotube, the slots having a circumferential arc about the tubular wall from about 150° to about 300°; and where adjacent slots are axially offset from one and the other from about 30° to about 60°. The second portion of the hypotube may be substantially free of any slots.

The hypotube may be formed from a metallic material, such as 316 or 304 stainless steel. In some embodiments, the first flexible portion of the hypotube has a bending radius of at least about 1.5 inches before plastic deformation. The tubular wall of the hypotube may have a thickness from about 0.005 inches to about 0.020 inches with an external diameter of the hypotube is from about 0.080 inches to about 0.260 inches. Advantageously, the slots have a kerf width from about 0.001 inches to about 0.003 inches.

The longitudinal distance between adjacent slots may be from about 0.010 inches to about 0.050 inches and/or from about ⅙ of the exterior diameter of the hypotube. The hypotube may have a longitudinal length from about 25 inches to about 40 inches with the flexible portion having a longitudinal length from about 15 inches to about 32 inches and/or about from about 50 percent to about 80 percent of the longitudinal length of the hypotube. In some embodiments, the hypotube includes an exterior surface having a surface finish of less than or equal to about 32 microinches RMS. The slots may have edges that are rounded to a radius of about 0.005 inches or less.

While the outer tubular sheath may include polymeric material, such as polytetrafluoroethylene, the hypotube is in some embodiments an uncoated hypotube free of any polymeric covering or liner.

When the hypotube is disposed within the outer tubular sheath, the hypotube may have a torqueability from about 70% to about 100%, where the torqueability is measured as ratio of rotation of the distal end of the hypotube for a rotation amount at the proximal end of the hypotube, when placed in a tortuous path, such as an S-shaped path having two full and opposed 180° bends with a bend radius of about 2 inches. In some embodiments, the torqueability of the hypotube is approximately or about 100% or a torqueability of about 1:1.

One particularly useful axial offset of the hypotube slots is about 45° so that the rotation of the device feels smooth when placed in a tortuous path, such as the above-described tortuous path. At axial offset angles greater than about 60°, rotation of the device becomes more granular which reduces feedback useful for accurate orientation of the device during delivery through bodily lumens.

In another aspect of the present invention an endovascular delivery system with an endovascular prosthesis is provided. The system may include an elongate outer tubular sheath having an open lumen and opposed proximal and distal ends with a medial portion therein between, the proximal end of the outer tubular sheath securably disposed to a first handle; an elongate inner metallic hypotube having a tubular wall with an open lumen and opposed proximal and distal ends with a medial portion therein between, the hypotube having a longitudinal length greater than a longitudinal length of the outer tubular sheath, the hypotube being slidably disposed within the open lumen of the outer tubular sheath, the proximal end of the hypotube securably disposed to a second handle; a delivery guide wire slidably disposed within the hypotube, a distal end of the delivery guidewire including an endovascular prosthesis releasably disposed thereat, the distal end of the delivery guidewire and the endovascular prosthesis being disposed past and beyond the distal end of the hypotube; the distal end of the outer tubular sheath being slidably disposed past and beyond the distal end of the hypotube to define an endovascular prosthesis delivery state and slidably retractable to the medial portion of the hypotube to define an endovascular prosthesis unsheathed state; where the hypotube further includes: a first flexible portion disposed from about the distal end of the hypotube to about the medial portion of the hypotube; a second portion disposed from about the medial portion of the hypotube to about the proximal end of the hypotube; the first flexible portion of the hypotube including a plurality of slots extending through the tubular wall of the hypotube, the slots having a circumferential arc about the tubular wall from about 150° to about 300°; and where adjacent slots are axially offset from one and the other from about 30° to about 60°. One particularly useful axial offset of the hypotube slots is about 45° so that the rotation of the device feels smooth when placed in a tortuous path, such as the above-described tortuous path. At axial offset angles greater than about 60°, rotation of the device becomes more granular which reduces feedback useful for accurate orientation of the device during delivery through bodily lumens.

The endovascular prosthesis may be an inflatable prosthesis. In some embodiments, the inflatable endovascular prosthesis is a bifurcated prosthesis having a tubular main body with an open end and two tubular legs. In some embodiments, the inflatable prosthesis includes inflatable cuffs disposed at the two tubular legs and the tubular main body. Furthermore, the tubular main body may further include an expandable stent disposed at the open end of the main tubular body. The second portion of the hypotube may be substantially free of any slots.

The hypotube may be formed from a metallic material, such as 316 or 304 stainless steel. In some embodiments, the first flexible portion of the hypotube has a bending radius of at least about 1.5 inches before plastic deformation. The tubular wall of the hypotube may have a thickness from about 0.005 inches to about 0.020 inches with an external diameter of the hypotube is from about 0.080 inches to about 0.260 inches. Advantageously, the slots have a kerf width from about 0.001 inches to about 0.003 inches.

The longitudinal distance between adjacent slots may be from about 0.010 inches to about 0.050 inches and/or from about ⅛th of the exterior diameter of the hypotube. The hypotube may have a longitudinal length from about 25 inches to about 40 inches with the flexible portion having a longitudinal length from about 15 inches to about 32 inches and/or about from about 50 percent to about 80 percent of the longitudinal length of the hypotube. In some embodiments, the hypotube includes an exterior surface having a surface finish of less than or equal to about 32 microinches RMS. The slots may have edges that are rounded to a radius of about 0.005 inches or less.

While the outer tubular sheath may include polymeric material, such as polytetrafluoroethylene, the hypotube is in some embodiments an uncoated hypotube free of any polymeric covering or liner.

When the hypotube is disposed within the outer tubular sheath, the hypotube may have a torqueability from about 70% to about 100%, where the torqueability is measured as ratio of rotation of the distal end of the hypotube for a rotation amount at the proximal end of the hypotube, when placed in a tortuous path. In some embodiments, the torqueability of the hypotube is approximately or about 100% or a torqueability of about 1:1.

In some aspects of the present invention, the endovascular prosthesis may be a modular endovascular graft assembly including a bifurcated main graft member formed from a supple graft material having a main fluid flow lumen therein. The main graft member may also include an ipsilateral leg with an ipsilateral fluid flow lumen in communication with the main fluid flow lumen, a contralateral leg with a contralateral fluid flow lumen in communication with the main fluid flow lumen and a network of inflatable channels disposed on the main graft member. The network of inflatable channels may be disposed anywhere on the main graft member including the ipsilateral and contralateral legs. The network of inflatable channels may be configured to accept a hardenable fill or inflation material to provide structural rigidity to the main graft member when the network of inflatable channels is in an inflated state. The network of inflatable channels may also include at least one inflatable cuff disposed on a proximal portion of the main graft member which is configured to seal against an inside surface of a patient's vessel. The fill material can also have transient or chronic radiopacity to facilitate the placement of the modular limbs into the main graft member. A proximal anchor member may be disposed at a proximal end of the main graft member and be secured to the main graft member. The proximal anchor member may have a self-expanding proximal stent portion secured to a self-expanding distal stent portion with struts having a cross sectional area that is substantially the same as or greater than a cross sectional area of proximal stent portions or distal stent portions adjacent the strut. At least one ipsilateral graft extension having a fluid flow lumen disposed therein may be deployed with the fluid flow lumen of the graft extension sealed to and in fluid communication with the fluid flow lumen of the ipsilateral leg of the main graft member. At least one contralateral graft extension having a fluid flow lumen disposed therein may be deployed with the fluid flow lumen of the graft extension sealed to and in fluid communication with the fluid flow lumen of the contralateral leg of the main graft member. For some embodiments, an outside surface of the graft extension may be sealed to an inside surface of the contralateral leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm, more specifically, about 3 cm to about 5 cm.

In another aspect of the present invention, a medical device is provided, where the medical device includes an elongate metallic hypotube having an open proximal end and an opposed open distal end defining a tubular wall having an open internal diameter and an exterior diameter; the tubular wall have a first flexible portion disposed near the proximal open end and a second portion disposed near the distal open end; where the first flexible portion of the hypotube includes a plurality of slots extending through the tubular wall and having a circumferential arc from about 150° to about 300°; and where adjacent slots are axially offset from one and the other from about 30° to about 60°. The second portion of the hypotube may be substantially free of any slots.

The hypotube may be formed from a metallic material, such as 316 or 304 stainless steel. In some embodiments, the first flexible portion of the hypotube has a bending radius of at least about 1.5 inches before plastic deformation. The tubular wall of the hypotube may have a thickness from about 0.005 inches to about 0.020 inches with an external diameter of the hypotube is from about 0.080 inches to about 0.260 inches. Advantageously, the slots have a kerf width from about 0.001 inches to about 0.003 inches.

The longitudinal distance between adjacent slots may be from about 0.010 inches to about 0.050 inches and/or from about 1/6 of the exterior diameter of the hypotube. The hypotube may have a longitudinal length from about 25 inches to about 40 inches with the flexible portion having a longitudinal length from about 15 inches to about 32 inches and/or about from about 50 percent to about 80 percent of the longitudinal length of the hypotube. In some embodiments, the hypotube includes an exterior surface having a surface finish of less than or equal to about 32 microinches RMS. The slots may have edges that are rounded to a radius of about 0.005 inches or less.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

BRIEF DESCRIPTION OF THE DRAWINGS

FIG. 11 is a top view of the hypotube of the present invention.

FIG. 12 is a front side view of the hypotube of the present invention.

DETAILED DESCRIPTION OF THE INVENTION

Embodiments of the invention are directed generally to methods and devices for treatment of fluid flow vessels with the body of a patient. Treatment of blood vessels is specifically indicated for some embodiments, and, more specifically, treatment of aneurysms, such as abdominal aortic aneurysms. With regard to graft embodiments discussed herein and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 1:
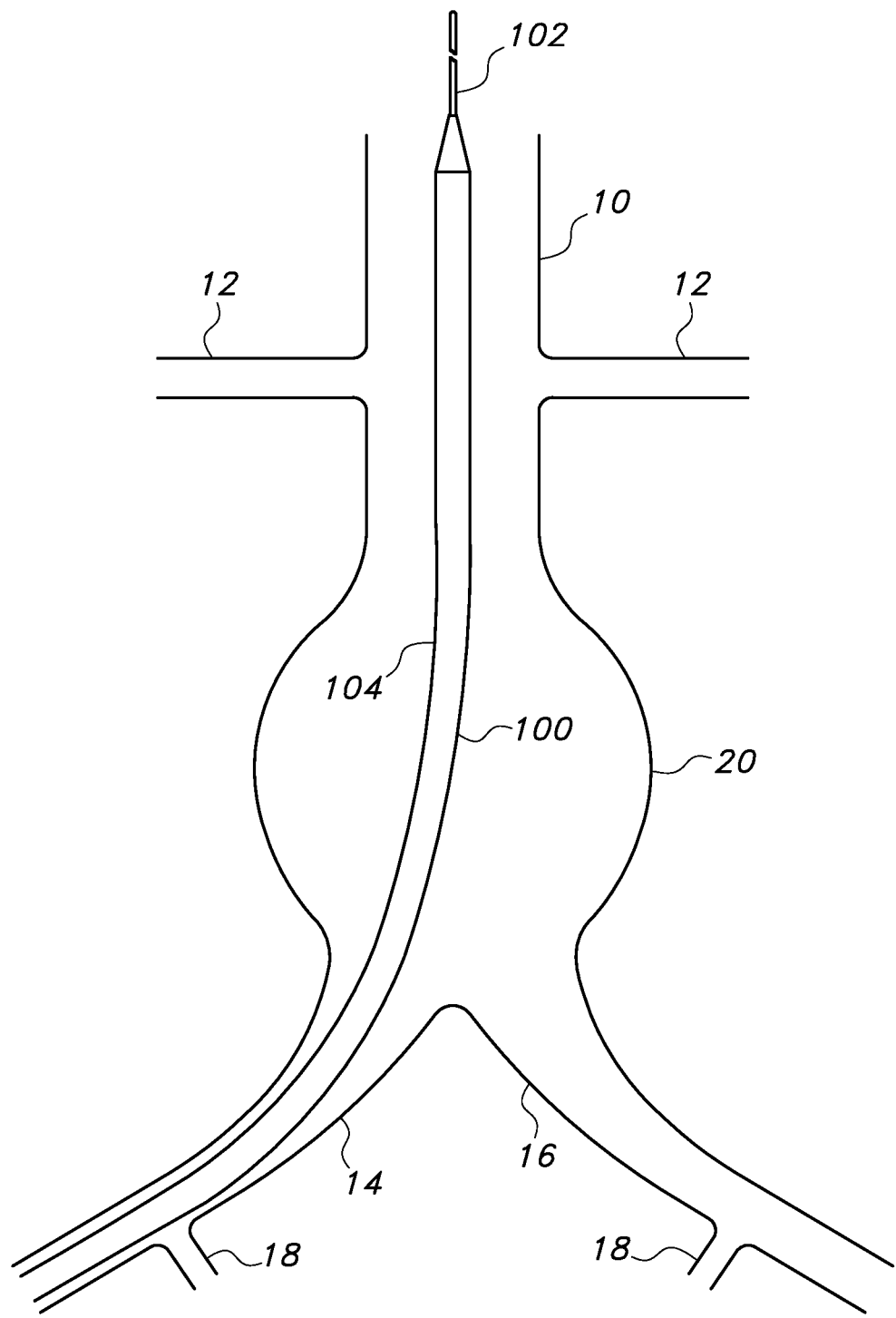
FIG. 1 depicts an initial deployment state of the endovascular delivery system of the present invention within a patient's vasculature.

FIG. 1 illustrates an embodiment of a deployment sequence of an embodiment of an endovascular prosthesis (not shown), such as a modular stent graft assembly. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter of the present invention may be directly inserted into the patient's access vessel by either arteriotomy or percutaneous puncture. Once the delivery sheath or sheaths have been properly positioned, an endovascular delivery catheter or system, typically containing an endovascular prosthesis such as but not limited to an inflatable stent-graft, may then be advanced over a guidewire through the delivery sheath and into the patient's vasculature.

FIG. 1 depicts the initial placement of the endovascular delivery system 100 of the present invention within a patient's vasculature. The endovascular delivery system 100 may be advanced along a guidewire 102 proximally upstream of blood flow into the vasculature of the patient including iliac arteries 14, 16 and aorta 10 shown in FIG. 1. While the iliac arteries 14, 16 may be medically described as the right and left common iliac arteries, respectively, as used herein iliac artery 14 is described as an ipsilateral iliac artery and iliac artery 16 is described as a contralateral iliac artery. The flow of the patient's blood (not shown) is in a general downward direction in FIG. 1. Other vessels of the patient's vasculature shown in FIG. 1 include the renal arteries 12 and hypogastric arteries 18.

The endovascular delivery system 100 may be advanced into the aorta 10 of the patient until the endovascular prosthesis (not shown) is disposed substantially adjacent an aortic aneurysm 20 or other vascular defect to be treated. The portion of the endovascular delivery system 100 that is advance through bodily lumens is in some embodiments a low profile delivery system; for example, having an overall outer diameter of less than 14 French. Other diameters are also useful, such as but not limited to less than 12 French, less than 10 French, or any sizes from 10 to 14 French or greater. Once the endovascular delivery system 100 is so positioned, an outer sheath 104 of the endovascular delivery system 100 may be retracted distally so as to expose the prosthesis (not shown) which has been compressed and compacted to fit within the inner lumen of the outer sheath 104 of the endovascular delivery system 100.

Figure 2:
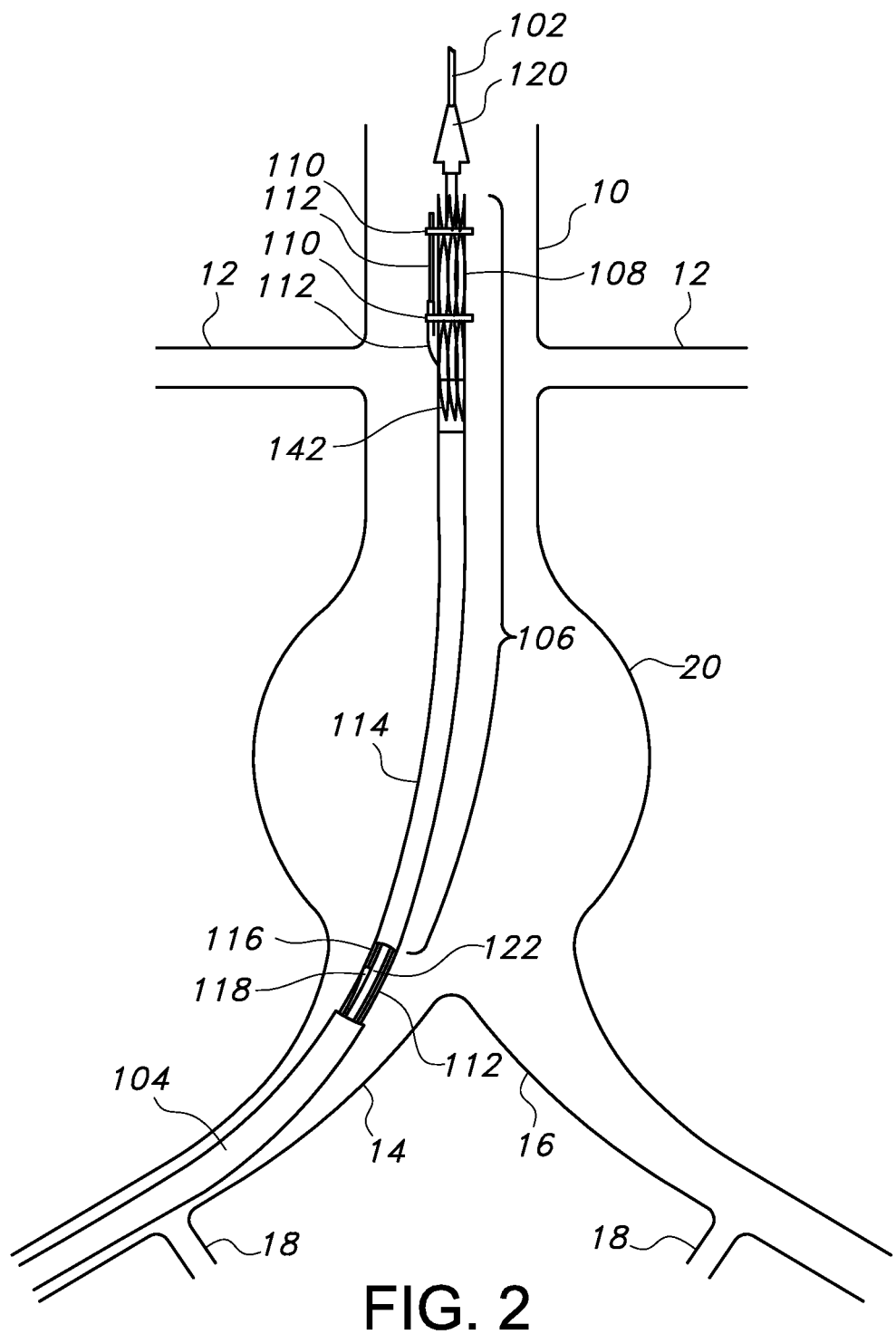
FIG. 2 depicts a deployment state of the endovascular delivery system of the present invention within a patient's vasculature after withdrawal of an outer sheath.

As depicted in FIG. 2, once the endovascular delivery system 100 is so positioned, the outer sheath 104 of the endovascular delivery system 100 may be retracted distally so as to expose the endovascular prosthesis 106 which has been compressed and compacted to fit within the inner lumen of the outer sheath 104 of the endovascular delivery system 100. The outer sheath 104 may be formed of a body compatible material. In some embodiments, the biocompatible material may be a biocompatible polymer. Examples of suitable biocompatible polymers may include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. In some embodiments, the biocompatible polymers include polypropylene (PP), polytetrafluoroethylene (PTFE), polyethylene terephthalate (PET), high density polyethylene (HDPE), combinations and copolymers thereof, and the like. Useful coating materials may include any suitable biocompatible coating. Non-limiting examples of suitable coatings include polytetrafluoroethylene, silicone, hydrophilic materials, hydrogels, and the like. Useful hydrophilic coating materials may include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylarnide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. In some embodiments, the outer sheath 104 may be made of polymeric materials, e.g., polyimides, polyester elastomers (Hytrel®), or polyether block amides (Pebax®), polytetrafluoroethylene, and other thermoplastics and polymers. The outside diameter of the outer sheath 104 may range from about 0.1 inch to about 0.4 inch. The wall thickness of the outer sheath 104 may range from about 0.002 inch to about 0.015 inch. The outer sheath 104 may also include an outer hydrophilic coating. Further, the outer sheath 104 may include an internal braided or otherwise reinforced portion of either metallic or polymeric filaments. In addition to being radially compressed when disposed within an inner lumen of the outer sheath 104 of the endovascular delivery system 100, a proximal stent 108 may be radially restrained by high strength flexible belts 110 in order to maintain a small profile and avoid engagement of the proximal stent 108 with a body lumen wall until deployment of the proximal stent 108 is initiated. The belts 110 can be made from any high strength, resilient material that can accommodate the tensile requirements of the belt members and remain flexible after being set in a constraining configuration. Typically, belts 110 are made from solid ribbon or wire of a shape memory alloy such as nickel titanium or the like, although other metallic or polymeric materials are possible. Belts 110 may also be made of braided metal filaments or braided or solid filaments of high strength synthetic fibers such as Dacron®, Spectra or the like. An outside transverse cross section of the belts 110 may range from about 0.002 to about 0.012 inch, specifically, about 0.004 to about 0.007 inch. The cross sections of belts 110 may generally take on any shape, including rectangular (in the case of a ribbon), circular, elliptical, square, etc. The ends of the belts 110 may be secured by one or more stent release wires or elongate rods 112 which extend through looped ends (not shown) of the belts 110. The stent release wires or elongate rods 112 may be disposed generally within the prosthesis 106 during delivery of the system 100 to the desired bodily location. For example, the stent release wires or elongate rods 112 may enter and exit the guidewire lumen 122 or other delivery system lumen as desired to affect controlled release of the stent 108, including if desired controlled and staged release of the stent 108. Once the outer sheath 104 of the endovascular delivery system 100 has been retracted, the endovascular delivery system 100 and the endovascular prosthesis 106 may be carefully positioned in an axial direction such that the proximal stent 108 is disposed substantially even with the renal arteries.

In some embodiments, the endovascular prosthesis 106 includes an inflatable graft 114. The inflatable graft may be a bifurcated graft having a main graft body 124, an ipsilateral graft leg 126 and a contralateral graft leg 128. The inflatable graft 114 may further include a fill port 116 in fluid communication with an inflation tube 118 of the endovascular delivery system 100 for providing an inflation medium (not shown). The distal portion of the endovascular delivery system 100 may include a nosecone 120 which provides an atraumatic distal portion of the endovascular delivery system 100. The guidewire 102 is slidably disposed within a guidewire lumen 122 of the endovascular delivery system 100.

Figure 3:
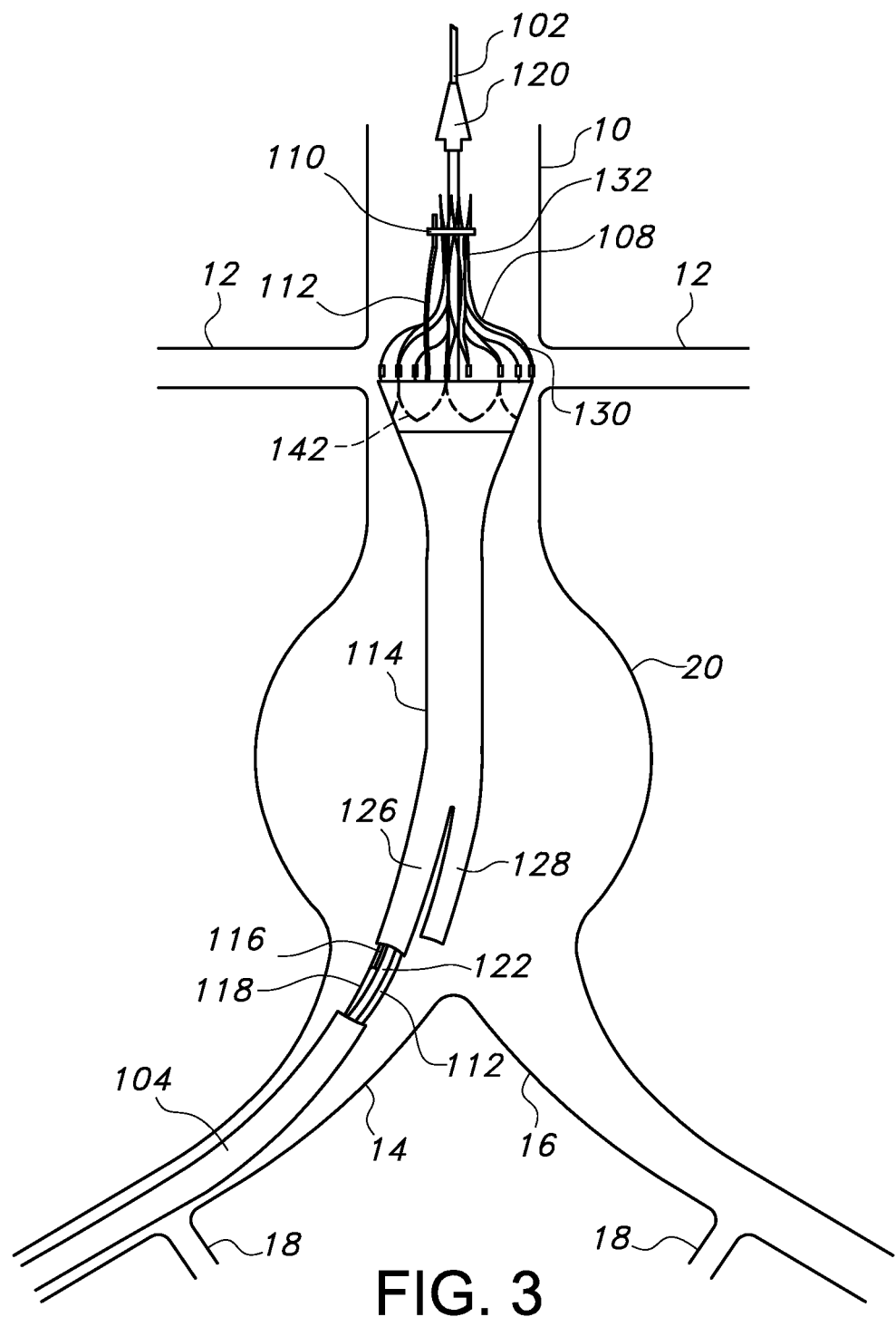
FIG. 3 depicts a deployment state of the endovascular delivery system of the present invention within a patient's vasculature after an initial and partial stent deployment.

As depicted in FIG. 3, deployment of the proximal stent 108 may begin with deployment of the distal portion 130 of stent 108 by retracting the stent release wire or rod 112 that couples ends of belt 110 restraining the distal portion 130 of the stent 108. The distal portion 130 of stent 108 may be disposed to the main graft body 124 via a connector ring 142. The stent 108 and/or the connector ring 142 may be made from or include any biocompatible material, including metallic materials, such as but not limited to, nitinol (nickel titanium), cobalt-based alloy such as Elgiloy, platinum, gold, stainless steel, titanium, tantalum, niobium, and combinations thereof. The present invention, however, is not limited to the use of such a connector ring 142 and other shaped connectors for securing the distal portion 130 of the stent 108 at or near the end of the main graft body 124 may suitably be used. Additional axial positioning typically may be carried out even after deploying the distal portion 130 of the stent 108 as the distal portion 130 may provide only partial outward radial contact or frictional force on the inner lumen of the patient's vessel or aorta 10 until the proximal portion 132 of the stent 108 is deployed. Once the belt 110 constraining the proximal portion 132 of the stent 108 has been released, the proximal portion 132 of the stent 108 self-expands in an outward radial direction until an outside surface of the proximal portion 132 of the stent 108 makes contact with and engages an inner surface of the patient's vessel 10.

Figure 4:
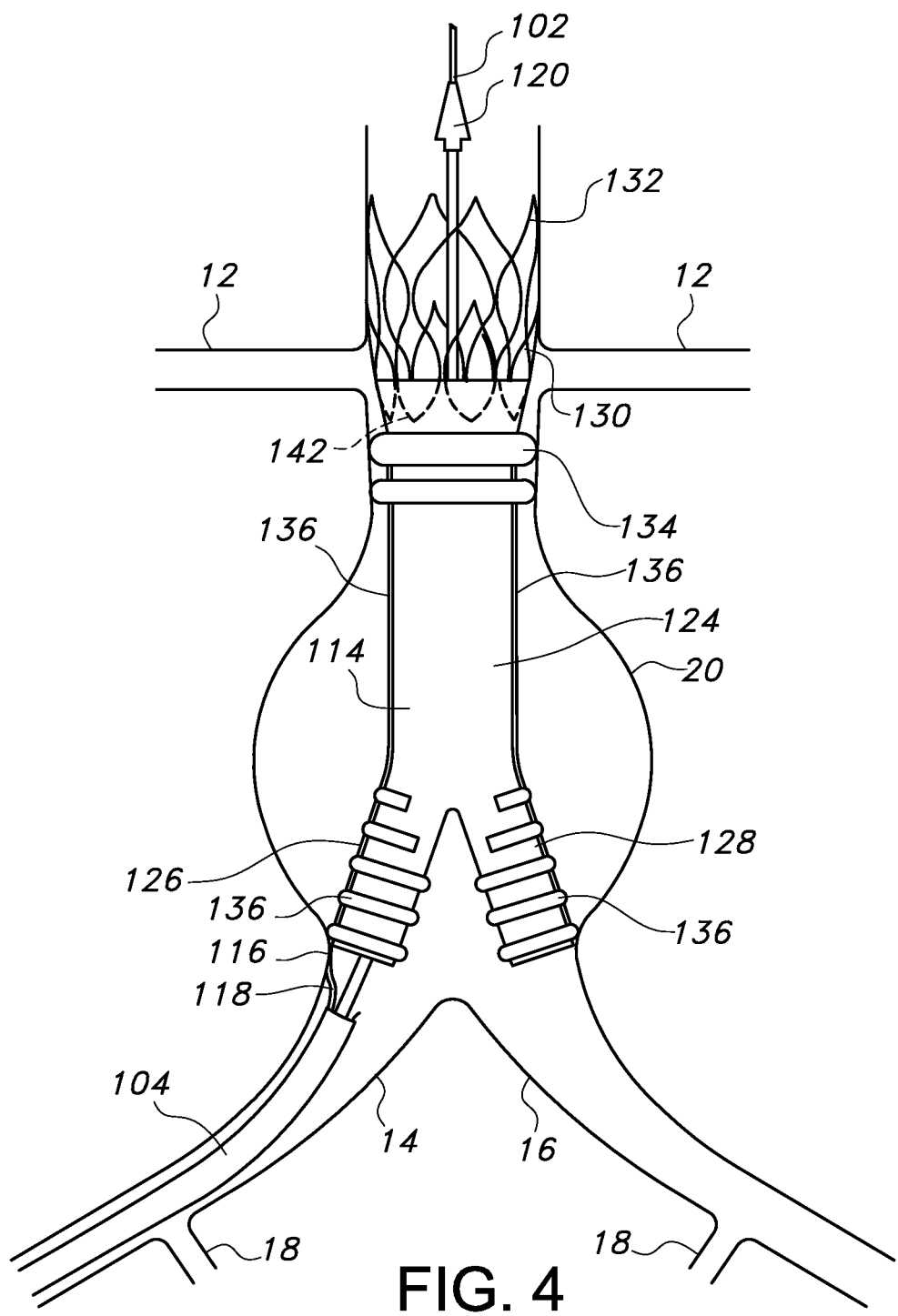
FIG. 4 depicts a deployment state of the endovascular delivery system of the present invention within a patient's vasculature after a stent deployment.

As depicted in FIG. 4, after the distal portion 130 of the stent 108 has been deployed, the proximal portion 132 of the stent 108 may then be deployed by retracting the wire 112 that couples the ends of the belt 110 restraining the proximal portion 132 of the stent 108. As the proximal portion 132 of the stent 108 self-expands in an outward radial direction, an outside surface of the proximal portion 132 of the stent 108 eventually makes contact with the inside surface of the patient's aorta 10. For embodiments that include tissue engaging barbs (not shown) on the proximal portion 132 of the stent 108, the barbs may also be oriented and pushed in a general outward direction so as to make contact and engage the inner surface tissue of the patient's vessel 10, which further secures the proximal stent 108 to the patient's vessel 10.

Once the proximal stent 108 has been partially or fully deployed, the proximal inflatable cuff 134 may then be filled through the inflation port 116 with inflation material injected through an inflation tube 118 of the endovascular delivery system 100 which may serve to seal an outside surface of the inflatable cuff 134 to the inside surface of the vessel 10. The remaining network of inflatable channels 136 may also be filled with pressurized inflation material at the same time which provides a more rigid frame like structure to the inflatable graft 114. For some embodiments, the inflation material may be a biocompatible, curable or hardenable material that may cured or hardened once the network of inflatable channels 136 are filled to a desired level of material or pressure within the network or after passage of a predetermined period of time. Some embodiments may also employ radiopaque inflation material to facilitate monitoring of the fill process and subsequent engagement of graft extensions (not shown). The material may be cured by any of the suitable methods discussed herein including time lapse, heat application, application of electromagnetic energy, ultrasonic energy application, chemical adding or mixing or the like. Some embodiments for the inflation material that may be used to provide outward pressure or a rigid structure from within the inflatable cuff 134 or network of inflatable channels 136 may include inflation materials formed from glycidyl ether and amine materials. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A (PO)$_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol r, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

The network of inflatable channels 136 may be partially or fully inflated by injection of a suitable inflation material into the main fill port 116 to provide rigidity to the network of inflatable channels 136 and the graft 114. In addition, a seal is produced between the inflatable cuff 134 and the inside surface of the abdominal aorta 10. Although it is desirable to partially or fully inflate the network of inflatable channels 136 of the graft 114 at this stage of the deployment process, such inflation step optionally may be accomplished at a later stage if necessary.

Figure 5:
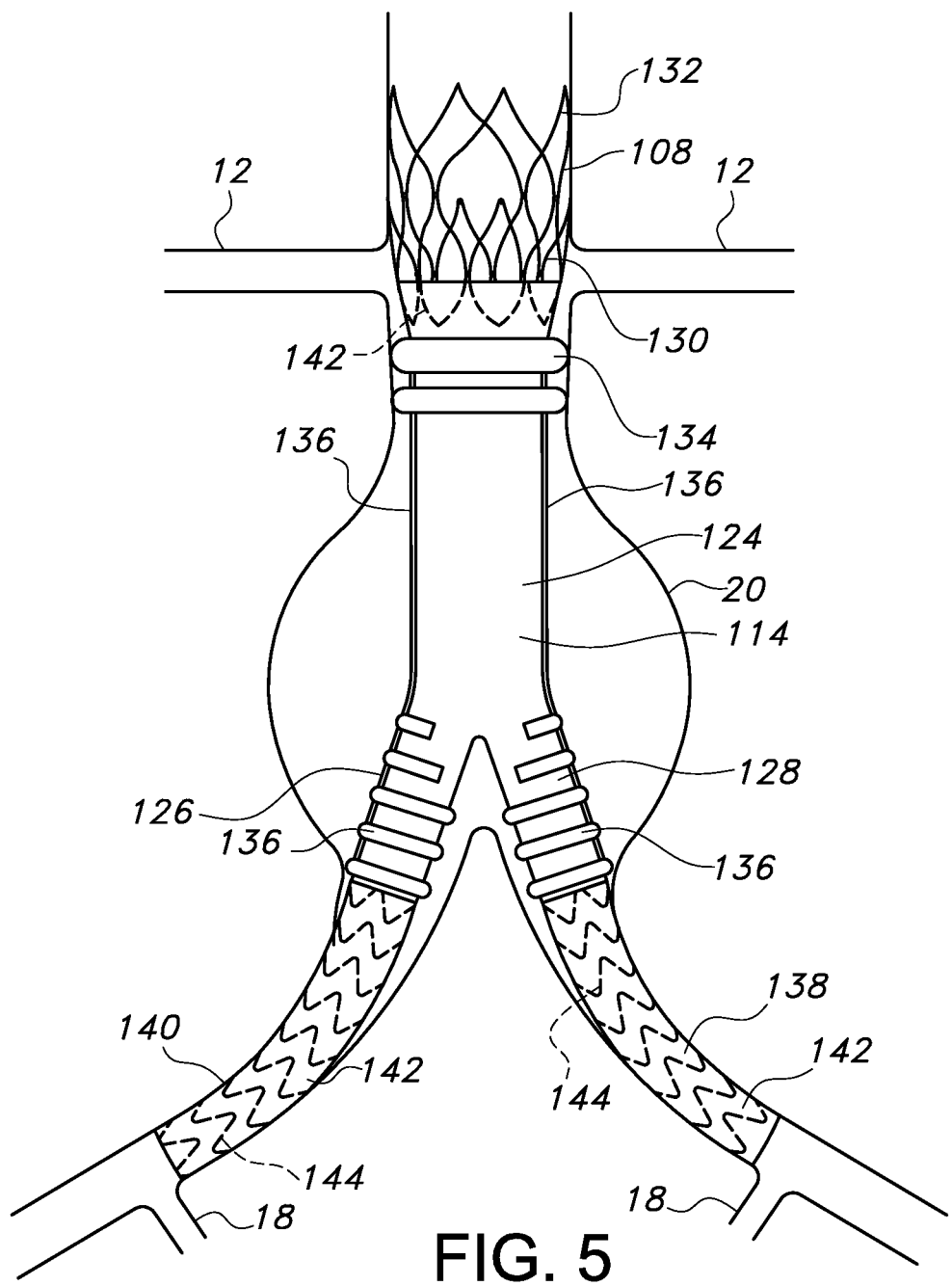
FIG. 5 depicts a deployed bifurcated endovascular prosthesis with graft leg extensions.

Once the graft 114 is deployed and the inflatable channels 136 thereof have been filled and expanded, another delivery catheter (not shown) may be used to deploy a contralateral graft extension 138, as depicted in FIG. 5. The contralateral graft extension 138 is in an axial position which overlaps the contralateral leg 128 of the graft 114. The amount of desired overlap of the graft extension 138 with the contralateral leg 128 may vary depending on a variety of factors including vessel morphology, degree of vascular disease, patient status and the like. However, for some embodiments, the amount of axial overlap between the contralateral graft extension 138 and the contralateral leg 128 may be about 1 cm to about 5 cm; more specifically, about 2 cm to about 4 cm. Once the contralateral graft extension 138 has been deployed, an ipsilateral graft extension 140 may be similarly deployed in the ipsilateral graft leg 126.

For some deployment embodiments, the patient's hypogastric arteries may be used to serve as a positioning reference point to ensure that the hypogastric arteries are not blocked by the deployment. Upon such a deployment, the distal end of a graft extension 138 or 140 may be deployed anywhere within a length of the ipsilateral leg 126 or contralateral leg 128 of the graft 114. Also, although only one graft extension 140, 138 is shown deployed on the ipsilateral side and contralateral side of the graft assembly 114, additional graft extensions 140, 138 may be deployed within the already deployed graft extensions 140, 138 in order to achieve a desired length extension of the ipsilateral leg 126 or contralateral leg 128. For some embodiments, about 1 to about 5 graft extensions 138, 140 may be deployed on either the ipsilateral or contralateral sides of the graft assembly 114. Successive graft extensions 138, 140 may be deployed within each other so as to longitudinally overlap fluid flow lumens of successive graft extensions.

Graft extensions 138, 140, which may be interchangeable for some embodiments, or any other suitable extension devices or portions of the main graft section 124 may include a variety of suitable configurations. For some embodiments, graft extensions 138, 140 may include a polytetrafluoroethylene (PTFE) graft 142 with helical nitinol stent 144.

Further details of the endovascular prosthesis 106 and/or graft extensions 138, 140 may be found in commonly owned U.S. Pat. Nos. 6,395,019; 7,081,129; 7,147,660; 7,147,661; 7,150,758; 7,615,071; 7,766,954 and 8,167,927 and commonly owned U.S. Published Application No. 2009/0099649, the contents of all of which are incorporated herein by reference in their entirety. Details for the manufacture of the endovascular prosthesis 106 may be found in commonly owned U.S. Pat. Nos. 6,776,604; 7,090,693; 7,125,464; 7,147,455; 7,678,217 and 7,682,475, the contents of all of which are incorporated herein by reference in their entirety. Useful inflation materials for the inflatable graft 114 may be found in may be found in commonly owned U.S. Published Application No. 2005/0158272 and 2006/0222596, the contents of all of which are incorporated herein by reference in their entirety. Additional details concerning delivery details, including systems, devices and methods, of the ipsilateral graft leg 126 and the contralateral leg 128 may be found in commonly owned U.S. Provisional Application No. 61/660,105, entitled "Bifurcated Endovascular Prosthesis Having Tethered Contralateral Leg", filed Jun. 15, 2012, the contents of which are incorporated the herein by reference in their entirety. Additional details of an endovascular delivery system having an improved radiopaque marker system for accurate prosthesis delivery may be found in commonly owned U.S. Provisional Application No. 61/660,413, entitled "Endovascular Delivery System With An Improved Radiopaque Marker Scheme", filed Jun. 15, 2012, the contents of which are incorporated the herein by reference in their entirety.

Useful graft materials for the endovascular prosthesis 106 include, but are not limited, polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. In some embodiments, the graft materials are non-textile graft materials, e.g., materials that are not woven, knitted, filament-spun, etc. that may be used with textile grafts. Such useful graft material may be extruded materials. Particularly useful materials include porous polytetrafluoroethylene without discernable node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. Such PTFE layers may lack distinct, parallel fibrils that interconnect adjacent nodes of ePTFE, typically have no discernable node and fibril microstructure when viewed at a magnification of up to 20,000. A porous PTFE layer having no or substantially no fluid permeability may have a Gurley Number of greater than about 12 hours, or up to a Gurley Number that is essentially infinite, or too high to measure, indicating no measurable fluid permeability. Some PTFE layers having substantially no fluid permeability may have a Gurley Number at 100 cc of air of greater than about $10^6$ seconds. The Gurley Number is determined by measuring the time necessary for a given volume of air, typically, 25 cc, 100 cc or 300 cc, to flow through a standard 1 square inch of material or film under a standard pressure, such as 12.4 cm column of water. Such testing maybe carried out with a Gurley Densometer, made by Gurley Precision Instruments, Troy, N.Y. Details of such useful PTFE materials and methods for manufacture of the same may be found in commonly owned U.S. Patent Application Publication No. 2006/0233991, the contents of which are incorporated herein by reference in their entirety.

Figure 6:
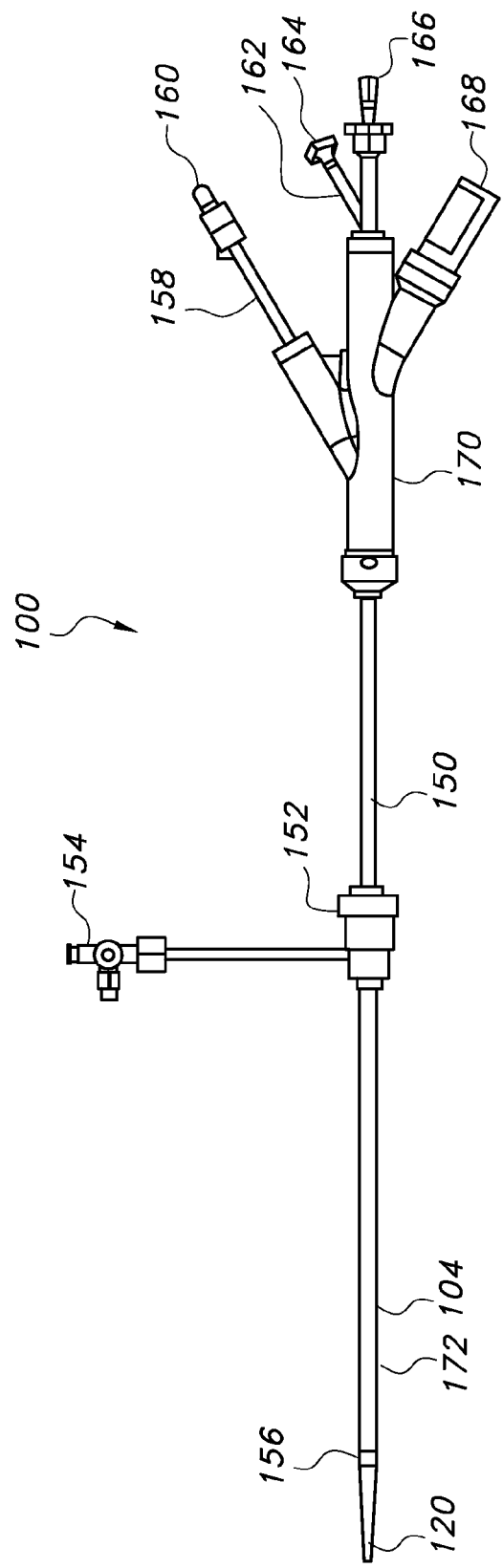
FIG. 6 is a side elevational view of the endovascular delivery system of the present invention.

FIG. 6 is a side elevational view of the endovascular delivery system 100 of the present invention. The endovascular delivery system 100 may include, among other things, the nosecone 120; the outer sheath 104; a retraction knob or handle 152 for the outer sheath 104; a flush port 154 for the outer sheath 104; an outer sheath radiopaque marker band 156; an inner tubular member or hypotube 150; an inflation material or polymer fill connector port 158; an inflation material or polymer fill cap 160; a guidewire flush port 162; a guidewire flush port cap 164; a guidewire port 166; and nested stent release knobs 168; interrelated as shown.

The flush port 154 for the outer sheath 104 may be used to flush the outer sheath 104 during delivery stages. The outer sheath 104 may have a radiopaque marker band to aid the practitioner in properly navigating the delivery system 100 to the desired bodily site. The outer sheath 104 is retractable by movement of the retraction knob or handle 152 for the outer sheath 104 by a practitioner towards the proximal handle assembly 170 of the delivery system 100. The inner tubular member or hypotube 150 is disposed from the inner tubular member or hypotube 150 toward a proximal portion of the delivery system 100. The inflation material or polymer fill connector port 158 and the inflation material or polymer fill cap 160 are useful for providing inflation material (e.g., polymeric fill material) to inflate proximal inflatable cuffs 134 and the network of inflatable channels 136 of the inflatable graft 114. The guidewire flush port 162 and the guidewire flush port cap 164 are useful for flushing the guidewire port 166 during delivery stages of the delivery system 100. The nested stent release knobs 168 contains a series of nested knobs (not shown) that that are used to engage release mechanisms for delivery of the endovascular prosthesis 106. Further details, including but not limited to methods, catheters and systems, for deployment of endovascular prostheses are disclosed in commonly owned U.S. Pat. Nos. 6,761,733 and 6,733,521 and commonly owned U.S. Patent Application Publication Nos. 2006/0009833 and 2009/0099649, all of which are incorporated by reference herein in their entirety.

Figure 7:
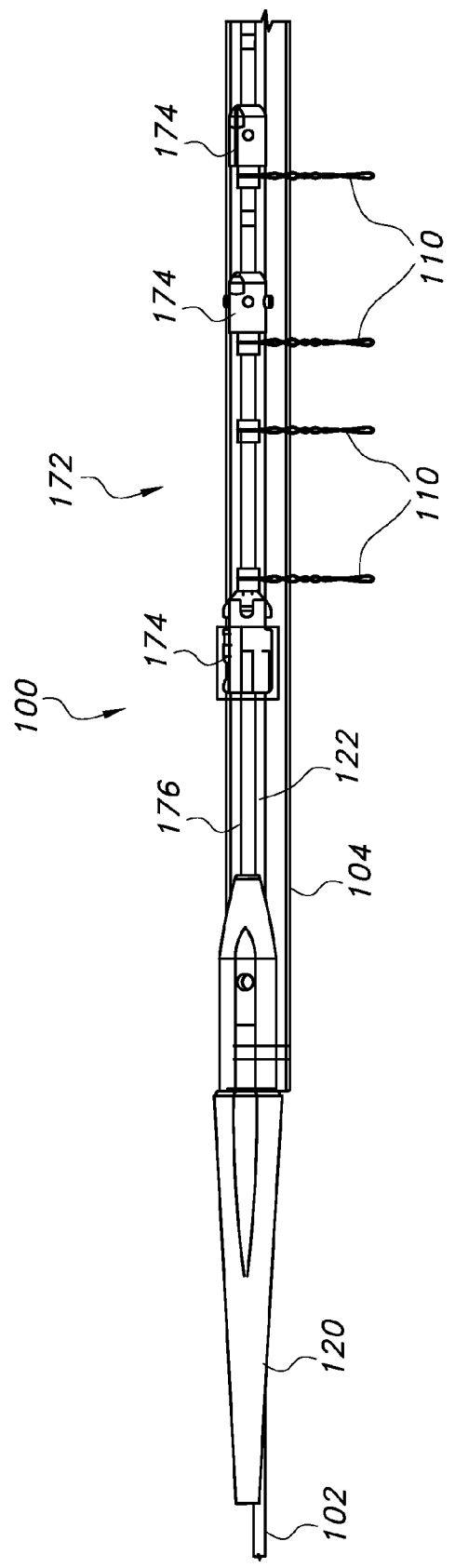
FIG. 7 is a side elevational and partial cutaway view of the distal portion of the endovascular delivery system of the present invention.
Figure 8:
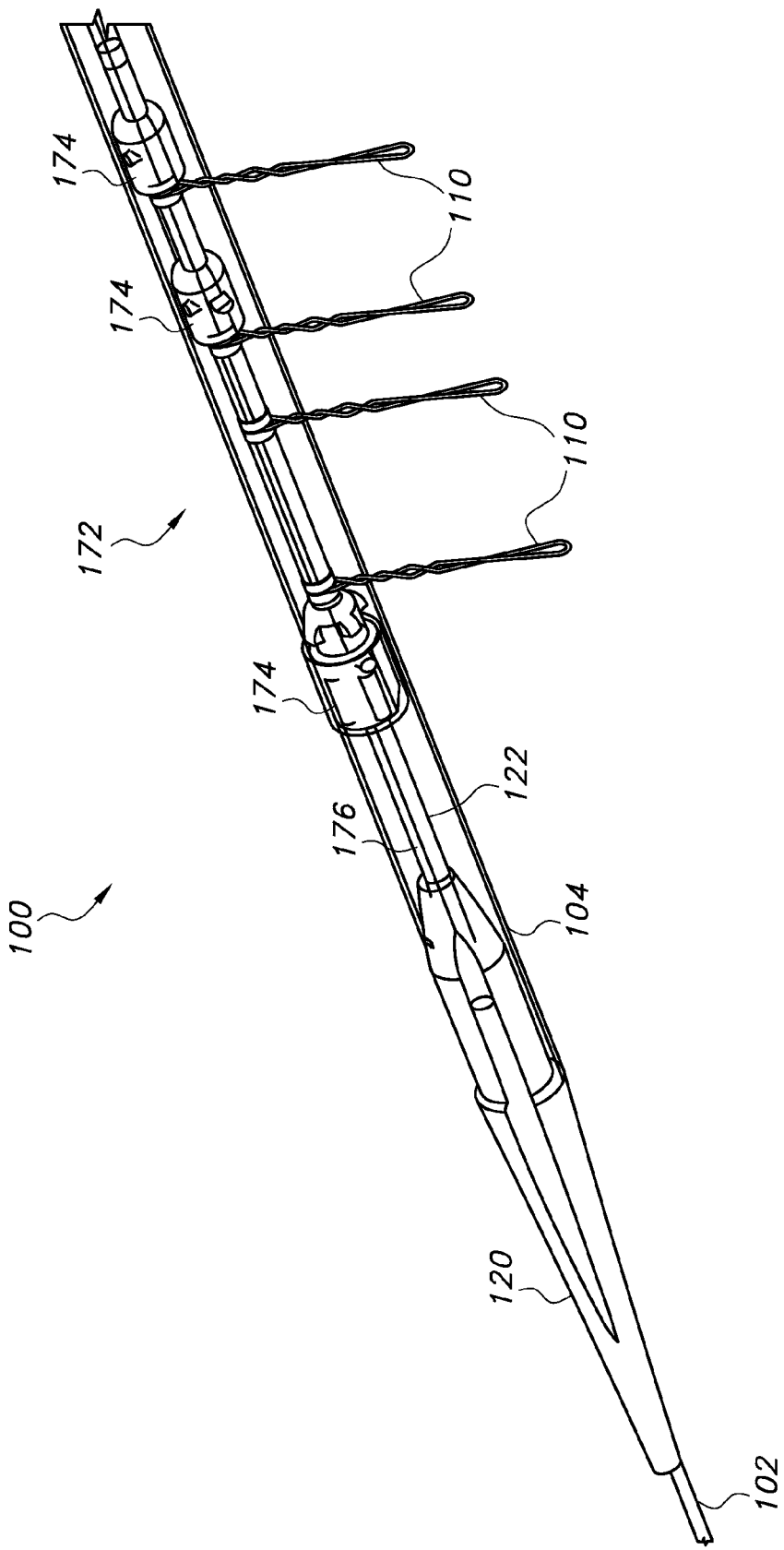
FIG. 8 is a partial perspective and partial cutaway view of the distal portion of the endovascular delivery system of the present invention.

FIG. 7 is a side elevational and partial cutaway view of the distal portion 172 of the endovascular delivery system 100 of the present invention, and FIG. 8 is a partial perspective and partial cutaway view of the distal portion 172 of the endovascular delivery system 100 of the present invention. The distal portion 172 of the endovascular delivery system 100 includes prosthesis/stent holders 174 disposed upon a prosthesis/stent holder guidewire 176. The holders 174 are useful releasably securing the endovascular prosthesis 106 (not shown) within the delivery system 100. The holders 174 inhibit or substantially inhibit undesirable longitudinal and/or circumferential movement of the endovascular prostheses 106 during delivery stages of the delivery system 100. Belts 110 serve to restrain the endovascular prosthesis 106 in a radially constrained stage until desired release of the endovascular prosthesis 106.

Figure 9:
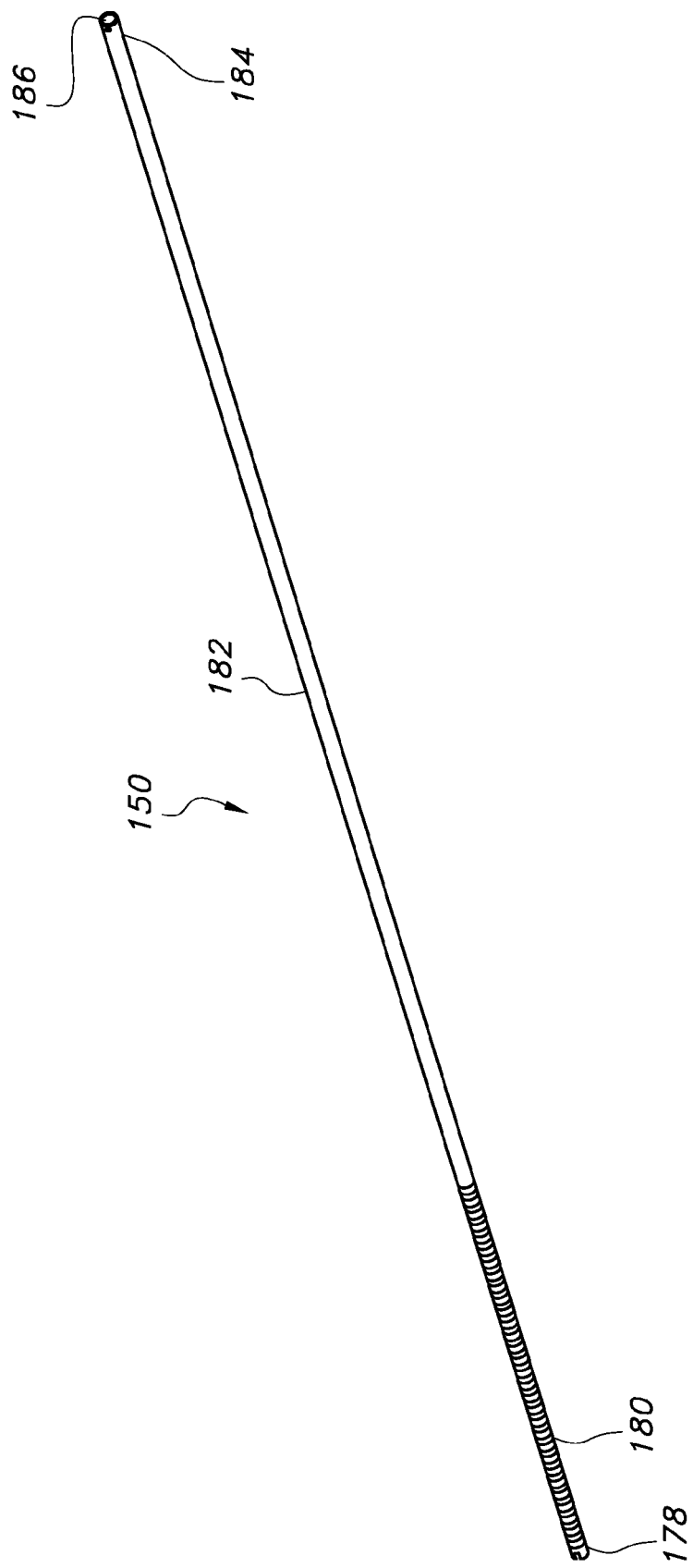
FIG. 9 is a perspective view of the inner tubular member or hypotube of the endovascular delivery system of the present invention.
Figure 10:
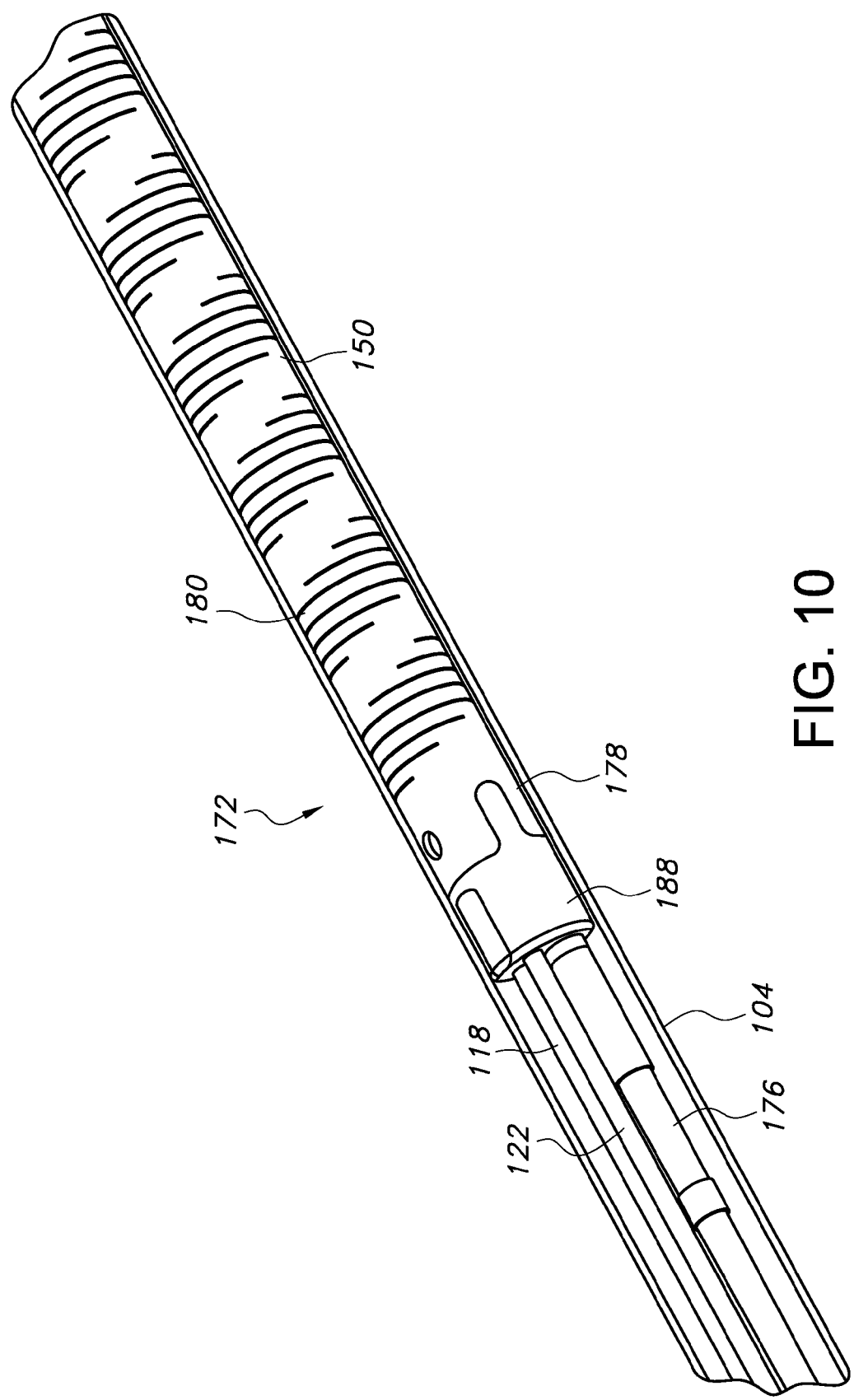
FIG. 10 is a partial perspective and cutaway view of a distal portion of the endovascular delivery system of the present invention showing a distal end portion of the hypotube.

FIG. 9 is a perspective view of an embodiment of the inner tubular member or hypotube 150 of the endovascular delivery system 100 of the present invention, and FIG. 10 is a partial perspective and cutaway view of a distal portion 172 of an embodiment of the endovascular delivery system 100 of the present invention showing a distal end 178 of the hypotube 150. The hypotube has an open lumen 186 and opposed distal end 178 and proximal end 184 with a medial portion 182 therein between. The proximal end 184 of the hypotube 150 is securable disposed to the proximal handle assembly 170. The distal end 178 of the hypotube 150 has a cap 188 through which the inflation tube 118, the guidewire lumen 122 and the prosthesis/stent holders guidewire 176 passes there through i.e., from the proximal handle assembly 170 and through the open lumen 186 of the hypotube 150. The cap 188 may be made from any polymeric or plastic material. Polycarbonate is an example of one useful material for the cap 188. The guidewire lumen 122 may be made from polymeric materials such as polyimide, polyethylene, polyetheretherketones (PEEK™), or other suitable polymers. The guidewire lumen 122 may have an outside diameter ranging from about 0.02 inch to about 0.08 inch and a wall thickness may range from about 0.002 inch to about 0.025 inch. Other lumens disposed within the lumen 186 of the hypotube 150 may be made from similar materials.

FIG. 11 is a top view of the hypotube of an embodiment of the present invention, and FIG. 12 is a front side view of an embodiment of the hypotube of the present invention. As depicted in FIGS. 11 and 12 the proximal and distal ends 184, 178 of the hypotube 150 have end slots 190 and end holes 192. Such end slots 190 and end holes 192 are useful for securing the proximal end 184 of the hypotube 150 to the proximal handle assembly 170 and for securing the distal end 178 of the hypotube 150 to the distal cap 188 of the hypotube 150. The end slots 190 are also useful for aligning the handle 170 to the device 100 such that the handle fill port 158 and the hypotube 150 are in the same plane but are offset at about 180° from each other.

Figure 13:
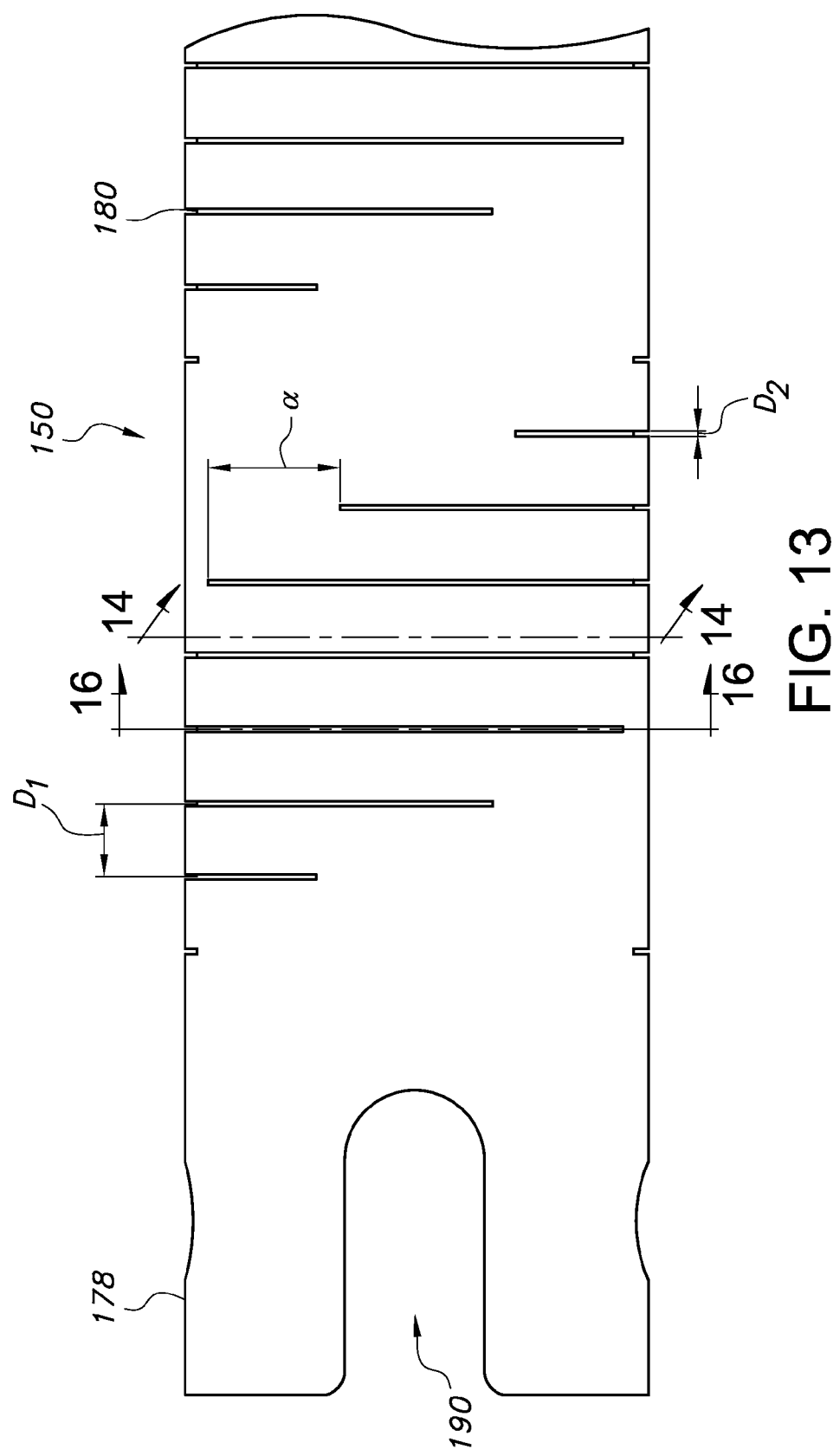
FIG. 13 is an exploded top view of the distal end of the hypotube of FIG. 11.

FIG. 13 is an exploded top view of the distal end of the hypotube of FIG. 11. As depicted in FIG. 13, the slots 180 may have a slot kerf $D_2$ width from about 0.0005 inches to about 0.0030 inches. In some embodiments, the slot kerf $D_2$ width is from about 0.0010 inches to about 0.0020 inches, more preferably about 0.0015±0.0010 inches. The longitudinal distance $D_1$ between adjacent slots 180 may be from about 0.010 inches to about 0.050 inches, preferably about 0.025±0.001 inches, or about ⅙ of the external diameter of the hypotube 150. Such dimensions are useful, for among other things, for a delivery system having an overall profile of about 14 French or less. The longitudinal distance $D_1$ may be increased to about 0.033 inches, allowing a reduction in the number of slots to reduce the cost and complexity of manufacturing the hypotube 150. The circumferential arc of the slots 180 (as represented by angle $\beta$ in FIG. 16) may be varied to obtain useful flexibility and torque performance or characteristics. Generally, increasing the circumferential arc will increase flexibility and torque performance or characteristics. The external diameter of the hypotube 150 may be from about 0.080 inches to about 0.260 inches, preferably about 0.156±0.001 inches. This external diameter is useful, for example, with delivery profiles of about 14 French or less and is non-limiting. Other external diameters may suitably be used. For example, one useful external diameter is about 0.134±0.001 inches for an overall low profile of about 12 French or less. The hypotube 150 may have a lumen wall thickness from about 0.005 inches to about 0.020 inches, including from about 0.005±0.001 inches to about 0.010±0.001 inches, and ±0.001. In some embodiments, the internal diameter of the hypotube 150 may be about 0.136±0.001 inches, resulting in a 0.010±0.001 inch wall thickness. This wall thickness is useful, for example, with delivery profiles of about 14 French or less and is non-limiting. Other wall thicknesses may suitably be used. For example, another useful thinner wall thickness of 0.005±0.001 inch may be used for an overall low profile of about 12 French or less. The overall longitudinal length of the hypotube 150 may vary from about 25 inches to about 40 inches. The overall longitudinal length of the flexible portion of the hypotube 150 having the slots 180 may vary from about 15 inches to about 32 inches.

Figures 14, 15:
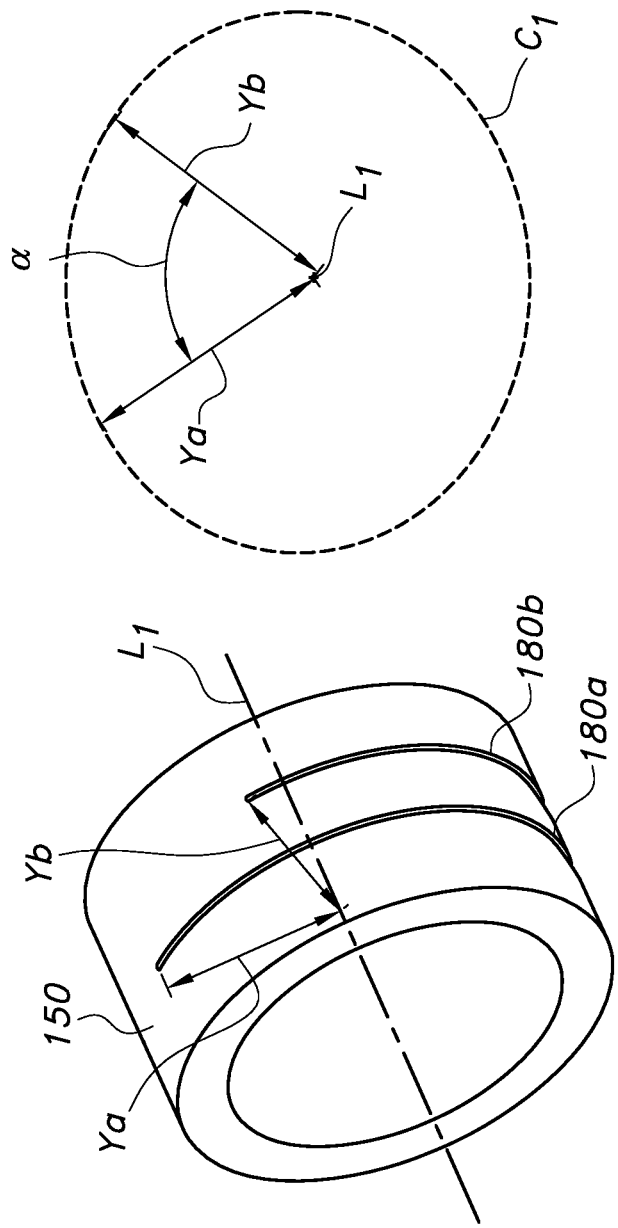
FIG. 14 is a partial perspective view an axial angular offset of adjacent slots of the hypotube of FIG. 13, taken along the 14-14 axis.
FIG. 15 is a planar schematic view of the axial angular offset of FIG. 14.

FIG. 14 is a partial perspective view an axial angular offset of adjacent slots of the hypotube of FIG. 13, taken along the 14-14 axis; and FIG. 15 is a planar schematic view of the axial angular offset of FIG. 14. In FIG. 15 the nominal circumference of the hypotube 150 is shown in outline by the dashed circle $C_1$. As depicted in FIGS. 14 and 15, adjacent slots 180a, 180b may be axially offset at an angle $\alpha$ from one and the other from about 30° to about 120°; preferably, from about 30° to about 90°; more preferably, from about 40° to about 50°. The axially offset angle $\alpha$ is defined as the angle between the slot end portions of the adjacent slots 180a, 180b from the longitudinal axis $L_1$ of the hypotube 150 as depicted by axes Ya, Yb, respectively. One useful axially offset angle $\alpha$ is about 45° for smooth rotation when placed in a tortuous path, such as tortuous path 198 described below in conjunction with FIG. 17.

Figure 16:
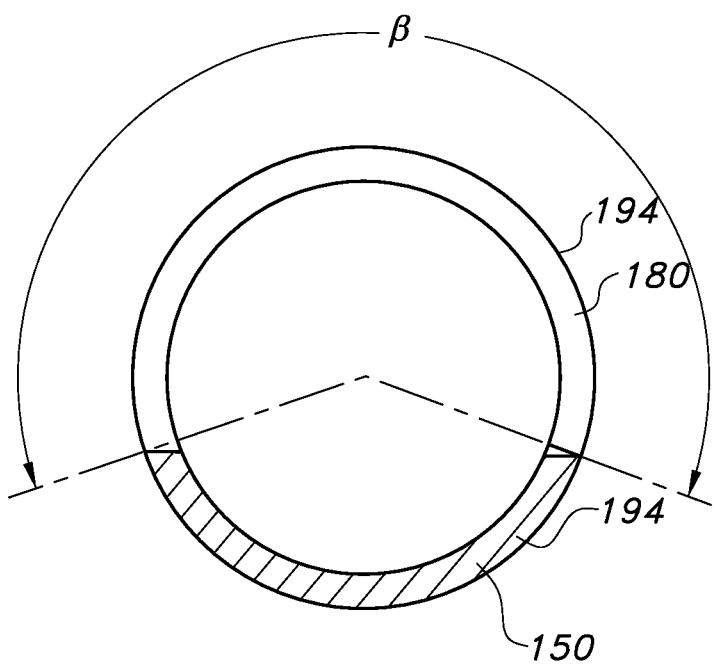
FIG. 16 is a cross-section view showing a slot circumference of the hypotube of FIG. 13, taken along the 16-16 axis.

FIG. 16 is a cross-section view showing a slot circumference of the hypotube of FIG. 13, taken along the 16-16 axis. As depicted in FIG. 16, the slots 180 may have a circumferential arc represented by an angle β from about 150° to about 300°. One useful circumferential arc or an angle β is about 220°±5°. This angle β is useful, but not limited to, for use with a wall thickness of about 0.010±0.001 inches. For thinner wall thicknesses, for example about 0.005±0.001 inches, a lower angle β of about 170°±5° may be used. Portions of the tubular wall 194 of the hypotube 150 that are outside of the circumferential arc of the slot 180 are shown in cross-hatch in FIG. 16.

While the slots 180 of the hypotube 150 have been described as being circumferential arcs, the present invention is not so limiting. The slots 180 may be, for example, generally circumferential. Such a general circumferential orientation may include a longitudinal extent along the longitudinal axis $L_1$ of the hypotube along with a circumferential extent along radial axis, $C_1$. In other words, a generally circumferential may include a helical orientation of the slots 180. Furthermore, the arcs themselves of the slots 180 may have different orientations, such as but not limited to a combination of circumferential and/or helical arcs including interleaving patterns, such as where the arcs or portions of the arcs may crisscross or be in a pattern of dual or more opposing helixes. Still furthermore, the slots 180 themselves may be angled through the wall of the hypotube 150. Moreover, portions of the slots 180 may not extend entirely through the wall of the hypotube 150, but may only extend partially from the outer surface of the hypotube 150 towards the inner surface of the hypotube 150, or vice versa, e.g. be a partial slot extending though only a portion of the hypotube wall where the slot opening stats at the outer surface of the hypotube, at the inner surfaces of the hypotube, or combinations thereof.

The hypotube 150 is in some embodiments an uncoated hypotube free of any polymeric covering or liner. One useful metallic material for the hypotube 150 may be 316 or 304 stainless steel. Other biocompatible materials may suitably be used, such as but not limited to, nitinol, cobalt-based alloy such as Elgiloy, platinum, gold, titanium, tantalum, niobium, and combinations thereof. The hypotube 150 may have a smooth exterior surface, such as one having a surface finish of less than or equal to about 32 microinches RMS. RMS is a measure of the smoothness of a surface. RMS refers to the Root Mean Square (RMS) of the average of measured peaks and valleys of a material surface profile calculated from a number of measurements along a sample length or area. Such RMS values are typically measured pursuant to ASTM D7127-015, the contents of which are incorporated herein by reference. RMS values from about 16 microinches to about 32 microinches are also useful. Moreover, the slots 180 have edges that are rounded to a radius of about 0.005 inches or less.

The hypotube 150 is in some embodiments may have a polymeric covering or liner. In some embodiments the polymeric covering or liner may be a polymer coating or a polymer extrusion. A polymer extrusion may cover the slit or slot 180 edges under bending. Such a covering significantly reduces the unsheathing forces in a tortuous path as compared to an uncoated hypotube and also provides hemostasis as the hypotube 150 is of the delivery system 100. A polymer coating will generally not cover the edges of the slits or slots 180. Such a polymer coating will reduce the unsheathing forces in a tortuous path as compared to an uncoated hypotube, but generally to a lesser degree as compared to a hypotube having the polymer extrusion. A hypotube with the polymer coating may not provide the degree of hemostasis as compared to the hypotube having the polymer extrusion. Both the hypotube having the polymer extrusion and the hypotube having the polymer coating will reduce the friction force through the flush port valve of the system 100, which also tends to reduce the unsheathing force. A hypotube with an inner polymer liner, which may be a polymer extrusion and/or a polymer coating, may be used to address or provide hemostasis.

Useful extrusion polymers include, but are not limited to, polytetrafluoroethylene (PTFE), ethylenetetrafluoroethylene (ETFE), fluorinated ethylene propylene (FEP), perfluoroalkoxy (PFA), polyethylene terephthalate (PET) and polyethylene co-extrusions. These extrusions polymers are heat-shrinkable. Useful thicknesses of the extrusion polymers include, but are not limited to, from about 0.0005 inches to about 0.002 inches. The thickness of the polymer coating may be less than about 0.0005 inches. The polymer coating may not actually cover the slits or slots 180, so as compared a hypotube having the polymer extrusion where the slit or slot 180 are covered, the polymer coated hypotube is not as "smooth" especially when hypotube is bent. Useful polymer coatings include, but are not limited to also, polytetrafluoroethylene (PTFE) and poly(p-xylylene) polymers (Parylene). Moreover, the hypotube 150 may be electro-polished to round the slit or slot edges, which also improves hypotube performance.

Figures 17, 18:
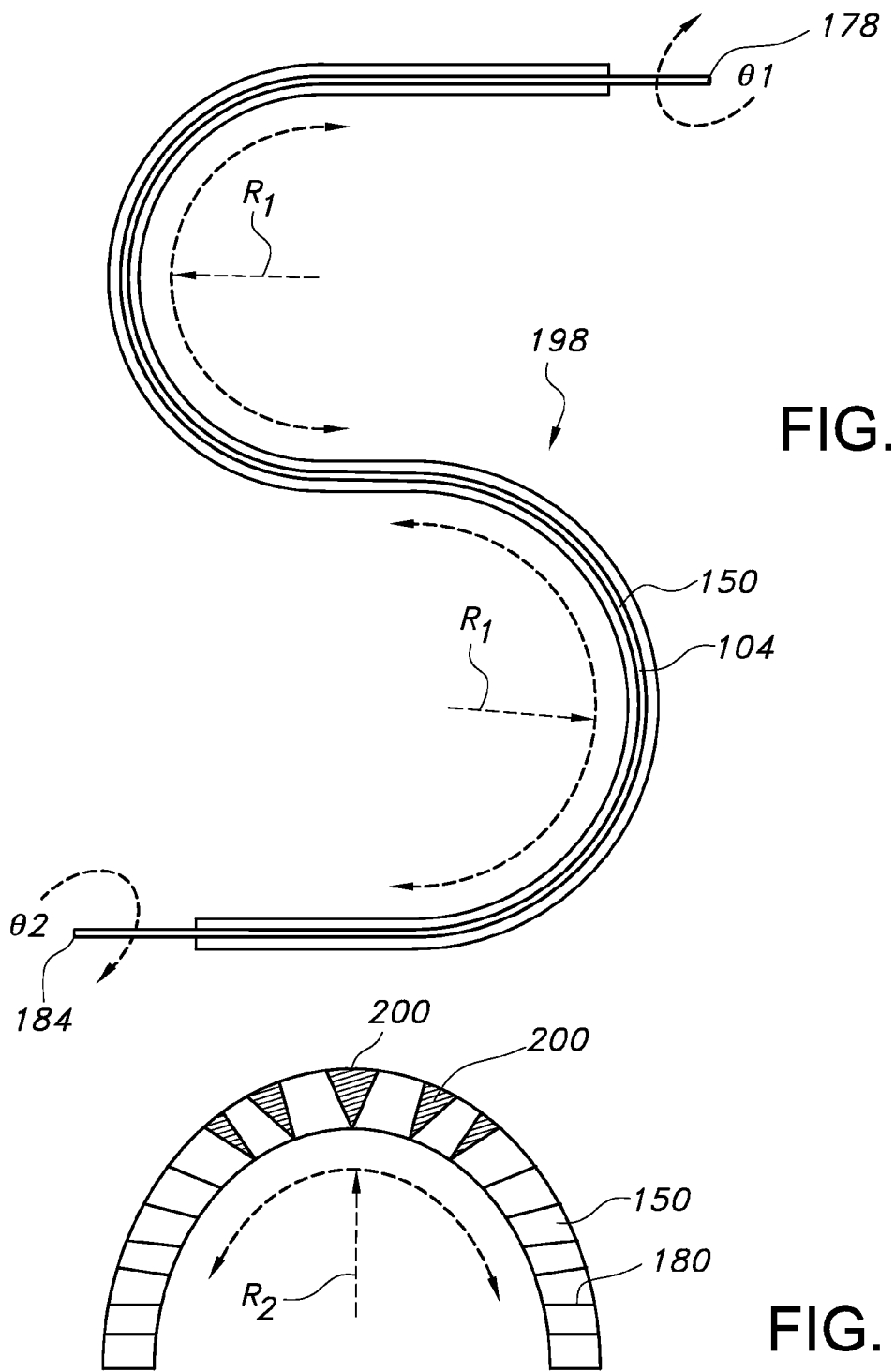
FIG. 17 is a schematic depiction of the hypotube of the present invention undergoing rotational torquing in a tortuous path.
FIG. 18 is a schematic depiction of the hypotube of the present invention undergoing deformation upon exceeding bending limits.

FIG. 17 is a schematic depiction of the hypotube of the present invention undergoing rotational torquing in a tortuous path 198. The tortuous path 198 is depicted in FIG. 17 as an S-shaped path having two full and opposed 180° bends with a bend radius $R_1$ of about 2 inches. With the hypotube 150 being disposed within the outer tubular sheath 104, the hypotube 150 has a torqueability from about 70% to about 100% when disposed in such a tortuous path 198. The torqueability is measured as percent of rotation of the distal end 178; i.e., angle θ1, of the hypotube 150 for a rotation amount at the proximal end 184; i.e., angle θ2, of the hypotube 150 when placed in the tortuous path 198. In some embodiments, the hypotube 150 has a torqueability of about 1:1 or 100% when disposed in such a tortuous path 198.

FIG. 18 is a schematic depiction of the hypotube of the present invention undergoing plastic deformation upon exceeding bending limits. As illustrated in FIG. 18, when the flexible portion of the hypotube 150 having the slots 180 is bent beyond a bending radius $R_2$ the material of the hypotube in the vicinity of certain slots, such as slots 200, may become plastically deformed. Such plastically deformation may prevent slots 200 returning completely to their original shape and orientation with the hypotube 150 after removal of a bending or other force. In some embodiments, the hypotube of the present invention has a bending radius $R_2$ of at least about 1.5 inches or no more than about 105 inches before portions of it may experience plastic deformation.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

The following embodiments or aspects of the invention may be combined in any fashion and combination and be within the scope of the present invention, as follows:

Embodiment 1

An endovascular delivery system, comprising:
an elongate outer tubular sheath having an open lumen and opposed proximal and distal ends with a medial portion therein between;
an elongate inner metallic hypotube having a tubular wall with an open lumen and opposed proximal and distal ends with a medial portion therein between, the hypotube having a longitudinal length greater than a longitudinal length of the outer tubular sheath, the hypotube being slidably disposed within the open lumen of the outer tubular sheath;
the distal end of the outer tubular sheath being slidably disposed past and beyond the distal end of the hypotube to define an endovascular prosthesis delivery state and slidably retractable to the medial portion of the hypotube to define an endovascular prosthesis unsheathed state;
wherein the hypotube further comprises:
a first flexible portion disposed from about the distal end of the hypotube to about the medial portion of the hypotube;
a second portion disposed from about the medial portion of the hypotube to about the proximal end of the hypotube;
the first flexible portion of the hypotube comprising a plurality of slots extending through the tubular wall of the hypotube, said slots having a circumferential arc about the tubular wall from about 150° to about 300°; and
wherein adjacent slots are axially offset from one and the other from about 30° to about 60°.

Embodiment 2

The endovascular delivery system of embodiment 1, wherein said hypotube is formed from a metallic material comprising 316 or 304 stainless steel.

Embodiment 3

The endovascular delivery system of embodiment 1, wherein the first flexible portion of the hypotube has a bending radius of no more than about 1.5 inches before plastic deformation.

Embodiment 4

The endovascular delivery system of embodiment 1, wherein the tubular wall of the hypotube has a thickness from about 0.005 inches to about 0.020 inches.

Embodiment 5

The endovascular delivery system of embodiment 1, wherein the external diameter of the hypotube is from about 0.080 inches to about 0.260 inches.

Embodiment 6

The endovascular delivery system of embodiment 1, wherein the slots have a kerf width from about 0.001 inches to about 0.003 inches.

Embodiment 7

The endovascular delivery system of embodiment 1, wherein a longitudinal distance between adjacent slots is from about 0.010 inches to about 0.050 inches.

Embodiment 8

The endovascular delivery system of embodiment 1, wherein a longitudinal distance between adjacent slots is from about ⅙ of the exterior diameter of the hypotube.

Embodiment 9

The endovascular delivery system of embodiment 1, wherein the hypotube comprises an exterior surface having a surface finish of less than or equal to about 32 microinches RMS.

Embodiment 10

The endovascular delivery system of embodiment 1, wherein the hypotube has a longitudinal length from about 25 inches to about 40 inches; and further wherein the flexible portion has a longitudinal length from about 15 inches to about 32 inches.

Embodiment 11

The endovascular delivery system of embodiment 1, wherein the hypotube has a longitudinal length; and further wherein the flexible portion has a longitudinal length from about 50 percent to about 80 percent of the longitudinal length of the hypotube.

Embodiment 12

The endovascular delivery system of embodiment 1, wherein the slots have edges that are rounded to a radius of about 0.005 inches or less.

Embodiment 13

The endovascular delivery system of embodiment 1, wherein the outer tubular sheath comprises polytetrafluoroethylene.

Embodiment 14

The endovascular delivery system of embodiment 1, wherein the hypotube is an uncoated hypotube free of any polymeric covering or liner.

Embodiment 15

The endovascular delivery system of embodiment 1, wherein, when the hypotube is disposed within the outer tubular sheath, the hypotube has a torqueability from about 70% to about 100%, said torqueability being measured as percent of rotation of the distal end of the hypotube for a rotation amount at the proximal end of the hypotube when placed in a tortuous path

Embodiment 16

The endovascular delivery system of embodiment 1, wherein, when the hypotube is disposed within the outer tubular sheath, the hypotube has a torqueability of about 1:1, said torqueability being measured as ratio of rotation of the distal end of the hypotube for a rotation amount at the proximal end of the hypotube, when placed in tortuous path.

Embodiment 17

The endovascular delivery system of embodiment 1, wherein the second portion of the hypotube is substantially free of any slots.

Embodiment 18

An endovascular delivery system, comprising:
- an elongate outer tubular sheath having an open lumen and opposed proximal and distal ends with a medial portion therein between, the proximal end of the outer tubular sheath securably disposed to a first handle;
- an elongate inner metallic hypotube having a tubular wall with an open lumen and opposed proximal and distal ends with a medial portion therein between, the hypotube having a longitudinal length greater than a longitudinal length of the outer tubular sheath, the hypotube being slidably disposed within the open lumen of the outer tubular sheath, the proximal end of the hypotube securably disposed to a second handle;
- a delivery guide wire slidably disposed within the hypotube, a distal end of the delivery guidewire including an endovascular prosthesis releasably disposed thereat, said distal end of the delivery guidewire and said endovascular prosthesis being disposed past and beyond the distal end of the hypotube;
- the distal end of the outer tubular sheath being slidably disposed past and beyond the distal end of the hypotube to define an endovascular prosthesis delivery state and slidably retractable to the medial portion of the hypotube to define an endovascular prosthesis unsheathed state;
- wherein the hypotube further comprises:
- a first flexible portion disposed from about the distal end of the hypotube to about the medial portion of the hypotube;
- a second portion disposed from about the medial portion of the hypotube to about the proximal end of the hypotube;
- the first flexible portion of the hypotube comprising a plurality of slots extending through the tubular wall of the hypotube, said slots having a circumferential arc about the tubular wall from about 150° to about 300°; and
- wherein adjacent slots are axially offset from one and the other from about 30° to about 60°.

Embodiment 19

The endovascular delivery system of embodiment 18, wherein said endovascular prosthesis is an inflatable prosthesis.

Embodiment 20

The endovascular delivery system of embodiment 19, wherein said inflatable endovascular prosthesis is a bifurcated prosthesis having a tubular main body with an open end and two tubular legs.

Embodiment 21

The endovascular delivery system of embodiment 20, wherein said inflatable prosthesis comprises inflatable cuffs disposed at said two tubular legs and said tubular main body.

Embodiment 22

The endovascular delivery system of embodiment 21, wherein said tubular main body further comprises an expandable stent disposed at said open end of said main tubular body.

Embodiment 23

The endovascular delivery system of embodiment 18, wherein said hypotube is formed from a metallic material comprising 316 or 304 stainless steel.

Embodiment 24

The endovascular delivery system of embodiment 18, wherein the first flexible portion of the hypotube has a bending radius of no more than about 1.5 inches before plastic deformation.

Embodiment 25

The endovascular delivery system of embodiment 18, wherein the tubular wall of the hypotube has a thickness from about 0.005 inches to about 0.020 inches.

Embodiment 26

The endovascular delivery system of embodiment 18, wherein the external diameter of the hypotube is from about 0.080 inches to about 0.260 inches.

Embodiment 27

The endovascular delivery system of embodiment 18, wherein the slots have a kerf width from about 0.001 inches to about 0.003 inches.

Embodiment 28

The endovascular delivery system of embodiment 18, wherein a longitudinal distance between adjacent slots is from about 0.010 inches to about 0.050 inches.

Embodiment 29

The endovascular delivery system of embodiment 18, wherein a longitudinal distance between adjacent slots is from about 1/6 of the exterior diameter of the hypotube.

Embodiment 30

The endovascular delivery system of embodiment 18, wherein the hypotube comprises an exterior surface having a surface finish of less than or equal to about 32 microinches RMS.

Embodiment 31

The endovascular delivery system of embodiment 18, wherein the hypotube has a longitudinal length from about 25 inches to about 40 inches; and further wherein the flexible portion has a longitudinal length from about 15 inches to about 32 inches.

Embodiment 32

The endovascular delivery system of embodiment 18, wherein the hypotube has a longitudinal length; and further wherein the flexible portion has a longitudinal length from about 50 percent to about 80 percent of the longitudinal length of the hypotube.

Embodiment 33

The endovascular delivery system of embodiment 18, wherein the slots have edges that are rounded to a radius of about 0.005 inches or less.

Embodiment 34

The endovascular delivery system of embodiment 18, wherein the outer tubular sheath comprises polytetrafluoroethylene.

Embodiment 35

The endovascular delivery system of embodiment 18, wherein the hypotube is an uncoated hypotube free of any polymeric covering or liner.

Embodiment 36

The endovascular delivery system of embodiment 18, wherein, when the hypotube is disposed within the outer tubular sheath, the hypotube has a torqueability from about 70% to about 100%, said torqueability being measured as percent of rotation of the distal end of the hypotube for a rotation amount at the proximal end of the hypotube when placed on tortuous path.

Embodiment 37

The endovascular delivery system of embodiment 18, wherein, when the hypotube is disposed within the outer tubular sheath, the hypotube has a torqueability of about 1:1, said torqueability being measured as ratio of rotation of the distal end of the hypotube for a rotation amount at the proximal end of the hypotube when placed on tortuous path.

Embodiment 38

The endovascular delivery system of embodiment 18, wherein the second portion of the hypotube is substantially free of any slots.

Embodiment 39

A medical device comprising:
an elongate metallic hypotube having an open proximal end and an opposed open distal end defining a tubular wall having an open internal diameter and an exterior diameter; said tubular wall have a first flexible portion disposed near the proximal open end and a second portion disposed near the distal open end;
wherein the first flexible portion of the hypotube comprises a plurality of slots extending through the tubular wall and having a circumferential arc from about 150° to about 300°; and
wherein adjacent slots are axially offset from one and the other from about 30° to about 60°.

Embodiment 40

The medical device of embodiment 39, wherein the hypotube comprises a metallic material.

Embodiment 41

The medical device of embodiment 40, wherein the metallic material comprises stainless steel.

Embodiment 42

The medical device of embodiment 40, wherein the metallic material is 316 or 304 stainless steel.

Embodiment 43

The medical device of embodiment 39, wherein the first flexible portion of the hypotube has a bending radius of no more than about 1.5 inches before plastic deformation.

Embodiment 44

The medical device of embodiment 39, wherein the tubular wall has a thickness from about 0.005 inches to about 0.020 inches.

Embodiment 45

The medical device of embodiment 39, the external diameter of the hypotube is from about 0.080 inches to about 0.260 inches.

Embodiment 46

The medical device of embodiment 39, wherein the slots have a kerf width from about 0.001 inches to about 0.003 inches.

Embodiment 47

The medical device of embodiment 39, wherein a longitudinal distance between adjacent slots is from about 0.010 inches to about 0.050 inches.

Embodiment 48

The medical device of embodiment 39, wherein a longitudinal distance between adjacent slots is from about ⅙ of the exterior diameter of the hypotube.

Embodiment 49

The medical device of embodiment 39, wherein the hypotube comprises an exterior surface having a surface finish of less than or equal to about 32 microinches RMS.

Embodiment 50

The medical device of embodiment 39, wherein the hypotube has a longitudinal length from about 25 inches to about 40 inches; and further wherein the flexible portion has a longitudinal length from about 15 inches to about 32 inches.

Embodiment 51

The medical device of embodiment 39, wherein the hypotube has a longitudinal length; and further wherein the flexible portion has a longitudinal length from about 50 percent to about 80 percent of the longitudinal length of the hypotube.

Embodiment 52

The medical device of embodiment 39, wherein the slots have edges that are rounded to a radius of about 0.005 inches or less.

Embodiment 53

The medical device of embodiment 39, wherein the second portion of the hypotube is substantially free of any slots.

What is claim is:

1. An endovascular delivery system, comprising:
an elongate outer tubular sheath having an open lumen and opposed proximal and distal ends with a medial portion therein between;
an elongate inner metallic hypotube having a tubular wall with an open lumen and opposed proximal and distal ends with a medial portion therein between, the hypotube having a longitudinal length greater than a longitudinal length of the outer tubular sheath, the hypotube being slidably disposed within the open lumen of the outer tubular sheath;
the distal end of the outer tubular sheath being slidably disposed past and beyond the distal end of the hypotube to define an endovascular prosthesis delivery state and slidably retractable to the medial portion of the hypotube to define an endovascular prosthesis unsheathed state;
wherein the hypotube further comprises:
a first flexible portion disposed from about the distal end of the hypotube to about the medial portion of the hypotube;
a second portion disposed from about the medial portion of the hypotube to about the proximal end of the hypotube;
the first flexible portion of the hypotube comprising a plurality of slots extending through the tubular wall of the hypotube, said slots having a circumferential arc about the tubular wall from about 150° to about 300°;
wherein adjacent slots are axially offset from one and the other from about 30° to about 60°;
wherein at least one end of the hypotube includes a hole for securement proximal to that end;
wherein the hypotube comprises an exterior surface having a surface finish of less than or equal to about 32 microinches RMS.

2. The endovascular delivery system of claim 1, wherein said hypotube is formed from a metallic material comprising 316 or 304 stainless steel.

3. The endovascular delivery system of claim 1, wherein the tubular wall of the hypotube has a thickness from about 0.005 inches to about 0.020 inches.

4. The endovascular delivery system of claim 1, wherein the slots have a kerf width from about 0.001 inches to about 0.003 inches.

5. The endovascular delivery system of claim 1, wherein a longitudinal distance between adjacent slots is from about 0.010 inches to about 0.050 inches.

6. The endovascular delivery system of claim 1, wherein the slots have edges that are rounded to a radius of about 0.005 inches or less.

7. The endovascular delivery system of claim 1, wherein the outer tubular sheath comprises polytetrafluoroethylene.

8. The endovascular delivery system of claim 1, wherein, when the hypotube is disposed within the outer tubular sheath, the hypotube has a torqueability from about 70% to about 100%, said torqueability being measured as percent of rotation of the distal end of the hypotube for a rotation amount at the proximal end of the hypotube when placed in a tortuous path.

9. An endovascular delivery system, comprising:
an elongate outer tubular sheath having an open lumen and opposed proximal and distal ends with a medial portion therein between, the proximal end of the outer tubular sheath securably disposed to a first handle;
an elongate inner metallic hypotube having a tubular wall with an open lumen and opposed proximal and distal ends with a medial portion therein between, the hypotube having a longitudinal length greater than a longitudinal length of the outer tubular sheath, the hypotube being slidably disposed within the open lumen of the outer tubular sheath, the proximal end of the hypotube securably disposed to a second handle, wherein said second handle comprises an inflation material fill port;
a delivery guide wire slidably disposed within the hypotube, a distal end of the delivery guidewire including an inflatable endovascular prosthesis releasably disposed thereat, said distal end of the delivery guidewire and said endovascular prosthesis being disposed past and beyond the distal end of the hypotube;
an inflation tube extending from the inflation material fill port and disposed within the hypotube;
a distal cap securably disposed at the distal end of the hypotube through which the inflation tube and the delivery guide wire passes there through to exit the hypotube;
the distal end of the outer tubular sheath being slidably disposed past and beyond the distal end of the hypotube to define an endovascular prosthesis delivery state and slidably retractable to the medial portion of the hypotube to define an endovascular prosthesis unsheathed state;
wherein the hypotube further comprises:
a first flexible portion disposed from about the distal end of the hypotube to about the medial portion of the hypotube;
a second portion disposed from about the medial portion of the hypotube to about the proximal end of the hypotube;
the first flexible portion of the hypotube comprising a plurality of slots extending through the tubular wall of the hypotube, said slots having a circumferential arc about the tubular wall from about 150° to about 300°;
at least one first elongate longitudinal slot disposed at the distal end of the hypotube;
at least one second elongate longitudinal slot disposed at the proximal end of the hypotube;
wherein adjacent slots are axially offset from one and the other from about 30° to about 60;
wherein, when the hypotube is disposed within the outer tubular sheath, the hypotube has a torqueability from about 70% to about 100%, said torqueability being measured as percent of rotation of the distal end of the hypotube for a rotation amount at the proximal end of the hypotube when placed on tortuous path; and
wherein the at least one first elongate longitudinal slot securably aligns the distal end of the hypotube to the distal cap and the at least one second elongate longitudinal slot securably aligns the proximal end of the hypotube to the second handle, thereby keeping the inflation material fill port in plane with the hypotube.

10. The endovascular delivery system of claim 9, wherein said inflatable endovascular prosthesis is a bifurcated prosthesis having a tubular main body with an open end and two tubular legs.

11. The endovascular delivery system of claim 10, wherein said inflatable prosthesis comprises inflatable cuffs disposed at said two tubular legs and said tubular main body.

12. The endovascular delivery system of claim 11, wherein said tubular main body further comprises an expandable stent disposed at said open end of said main tubular body.

13. The endovascular delivery system of claim 9, wherein said hypotube is formed from a metallic material comprising 316 or 304 stainless steel.

14. The endovascular delivery system of claim 9, wherein the first flexible portion of the hypotube has a bending radius of no more than about 1.5 inches before plastic deformation.

15. The endovascular delivery system of claim 9, wherein the tubular wall of the hypotube has a thickness from about 0.005 inches to about 0.020 inches.

16. The endovascular delivery system of claim 9, wherein the slots have a kerf width from about 0.001 inches to about 0.003 inches.

17. The endovascular delivery system of claim 9, wherein a longitudinal distance between adjacent slots is from about 0.010 inches to about 0.050 inches.

18. The endovascular delivery system of claim 9, wherein the hypotube comprises an exterior surface having a surface finish of less than or equal to about 32 microinches RMS.

19. The endovascular delivery system of claim 9, wherein the slots have edges that are rounded to a radius of about 0.005 inches or less.

20. The endovascular delivery system of claim 9, wherein the outer tubular sheath comprises polytetrafluoroethylene.

21. The endovascular delivery system of claim 9, wherein the hypotube is an uncoated hypotube free of any polymeric covering or liner.

22. The endovascular delivery system of claim 9, wherein the hypotube has a polymeric covering of a polymer coating or a polymer extrusion.

* * * * *